United States Patent
Shur et al.

(10) Patent No.: US 7,439,221 B2
(45) Date of Patent: Oct. 21, 2008

(54) METHODS AND COMPOSITIONS FOR MODULATING GAMETE ADHESION

(75) Inventors: Barry D. Shur, Atlanta, GA (US); Michael Ensslin, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 10/575,816

(22) PCT Filed: Oct. 18, 2004

(86) PCT No.: PCT/US2004/034391

§ 371 (c)(1),
(2), (4) Date: Nov. 9, 2006

(87) PCT Pub. No.: WO2005/037229

PCT Pub. Date: Apr. 28, 2005

(65) Prior Publication Data

US 2007/0169210 A1    Jul. 19, 2007

Related U.S. Application Data

(60) Provisional application No. 60/512,174, filed on Oct. 17, 2003.

(51) Int. Cl.
*C07K 14/00* (2006.01)
(52) U.S. Cl. .......................... 514/2; 530/350
(58) Field of Classification Search ............ 512/2; 530/350
See application file for complete search history.

(56) References Cited

U.S. PATENT DOCUMENTS 5,972,337 A * 10/1999 Ceriani et al. ............ 424/185.1

FOREIGN PATENT DOCUMENTS

| EP | 1 004 644 | * | 2/2000 |
| WO | WO 03/016522 | * | 2/2003 |

OTHER PUBLICATIONS

Kanai et al. 2000; Identification of a stromal cell type characterized by the secretion of a soluble integrin-binding protein, MFG-E8, in mouse early gonadogenesis. Mechanisms of Development 96: 223-227.*
Stubbs et al. (1990; cDNA cloning of a mouse mammary epithelial cell surface protein reveals the existence of epidermal growth factor-like domains linked to factor VIII-lie sequences. PNAS 87:8417-8421.*
Ogura et al. 1996; Cloning and expression of cDNA for O-acetylation of GD3 ganglioside. Biochem. Biophys Res. Commun. 225: 932-938.*
Oshima et al. Feb. 2002; Secretion of a peripheral membrane protein, MFG-E8, as a complex with membrane vesicles: a possible role in membrane secretion. Eur. J. Biochem. 269: 1209-1218.*

* cited by examiner

*Primary Examiner*—Karen Cochrane Carlson
(74) *Attorney, Agent, or Firm*—Thomas, Kayden, Horstemeyer & Risley, LLP

(57) ABSTRACT

Methods and compositions for modulating mammalian gamete adhesion are provided. Representative modulators of gamete adhesion include, but are not limited to polypeptides comprising at least one discoidin/C domain, and optionally at least one EGF domain. A representative polypeptide includes, but is not limited to SED1 polypeptides (SEQ ID NOs. 2-7), prodrugs, fragments, or derivatives thereof. Methods for identifying modulators of SED1-mediated gamete adhesion are also provided.

5 Claims, 8 Drawing Sheets

METHODS AND COMPOSITIONS FOR MODULATING GAMETE ADHESION

CROSS-REFERENCE TO RELATED APPLICATIONS

This application is a national stage application of PCT/US04/34391, filed Oct. 18, 2004, which claims benefit of and priority to U.S. Provisional Patent entitled "Therapeutic Applications of SED1" Application No. 60/512,174 filed on Oct. 17, 2003, and where permissible, is incorporated by reference in its entirety.

STATEMENT REGARDING FEDERALLY SPONSORED RESEARCH OR DEVELOPMENT

Aspects of this disclosure were supported in part by the National Institutes of Health Grant No. HD23479. The United States Government may have certain rights with respect to the claimed subject matter.

BACKGROUND

About 15% of couples have reduced fertility and approximately one-half of these are due to male infertility, usually of genetic origin. Common treatments include drug therapy, surgery, testicular sperm extraction (TESE) and magnelaser therapy. Genetic defects are believed to be the most prevalent cause of abnormalities, which result in the loss of specific DNA segments and ultimately leads to loss of vital genes for sperm production.

There are several technologies currently under development that target male infertility, including recombinant human zona pellucida protein (rhZP3) and glycosylated peptides having biological activity of binding to human spermatozoa, a TIAP polypeptide, and use of N-acetyl-L-cysteine to treat and prevent inflammation-based infertility.

Addressing male contraception is a much trickier subject since men produce approximately 100 million sperm every day, compared to women, who typically produce one functional gamete per month. There are numerous ongoing efforts aimed at male contraception. Such research includes attempting to elucidate the underlying molecular mechanism of fertilization.

Successful fertilization in mammals is dependent upon the species-specific recognition, adhesion, and fusion between sperm and egg. Despite their fundamental importance, little is known about the molecular basis underlying these events. Two sperm-egg recognition events in particular have received the most attention: the initial adhesion between the sperm plasma membrane and the egg extracellular coat, or zona pellucida, and the binding between membranes of the acrosome-reacted sperm and the egg plasma membrane (Primakoff and Myles, 2002; Wassarman et al., 2001). In both instances, candidate receptors have been identified, but thus far, none of these receptors appear to be completely responsible for either sperm-egg binding or sperm-egg fusion (Miller et al., 1992; Nishimura et al., 2001; Rankin et al., 1998). In particular, sperm binding to the zona pellucida is thought to involve recognition of specific glycoside residues on the ZP3 glycoprotein (Florman and Wassarman, 1985), which lead to aggregation of the sperm receptor and trigger acrosomal exocytosis. The nature of the sperm binding oligosaccharides on ZP3 remains unclear, as are the sperm proteins that bind ZP3 (Florman and Wassarman, 1985; Johnston et al., 1998; Miller et al., 1992; Nagdas et at., 1994; Nishimura et al., 2001; Primakoff and Myles, 2002; Rankin et al., 1998; Wassarman et al., 2001).

One candidate that has been extensively studied is $\beta 1,4$-galactosyltransferase I (GalT I). A wealth of evidence suggests that GalT I functions as a ZP3 receptor and participates in G protein-dependent acrosomal exocytosis following ZP3-mediated GalT I aggregation (Gong et al., 1995; Miller et al., 1992). In this regard, ectopic expression of GalT I on Xenopus oocytes leads to specific ZP3 binding and G protein activation. Site-directed mutagenesis of the GalT I cytoplasmic domain prevents ZP3-dependent G protein activation (Shi et al., 2001). Furthermore, overexpression of GalT I on mouse sperm leads to increased ZP3 binding, G protein activation, and accelerated acrosomal exocytosis (Youakim et al., 1994), whereas GalT I deletion leads to a loss of ZP3 binding and a concomitant loss of zona-induced acrosome reactions (Lu and Shur, 1997). Nevertheless, GalT I null sperm are still able to adhere to the egg coat and fertilize the egg, albeit at low efficiency, although they no longer bind ZP3 (Lu and Shur, 1997). This indicates that sperm adhesion to the zona pellucida requires receptors in addition to GalT I and ZP3, consistent with results from others (Rankin et al., 1998, 2003).

SUMMARY

The disclosure generally provides methods and compositions for modulating mammalian gamete adhesion. The methods and compositions may be used for both diagnostic and therapeutic purposes. Representative modulators of gamete adhesion include, but are not limited to, polypeptides comprising at least one discoidin/C domain, and optionally at least one EGF domain. A representative polypeptide includes, but is not limited to, SED1 polypeptides (SEQ ID NOs. 2-7), prodrugs, fragments, or derivatives thereof.

Another aspect of the disclosure provides a method for modulating mammalian gamete adhesion by administering to a host an amount of a gamete adhesion modulator effective to modulate SED1-mediated gamete adhesion.

Still other aspects provide methods for identifying modulators of SED1-mediated gamete adhesion.

DETAILED DESCRIPTION

Figure 1:
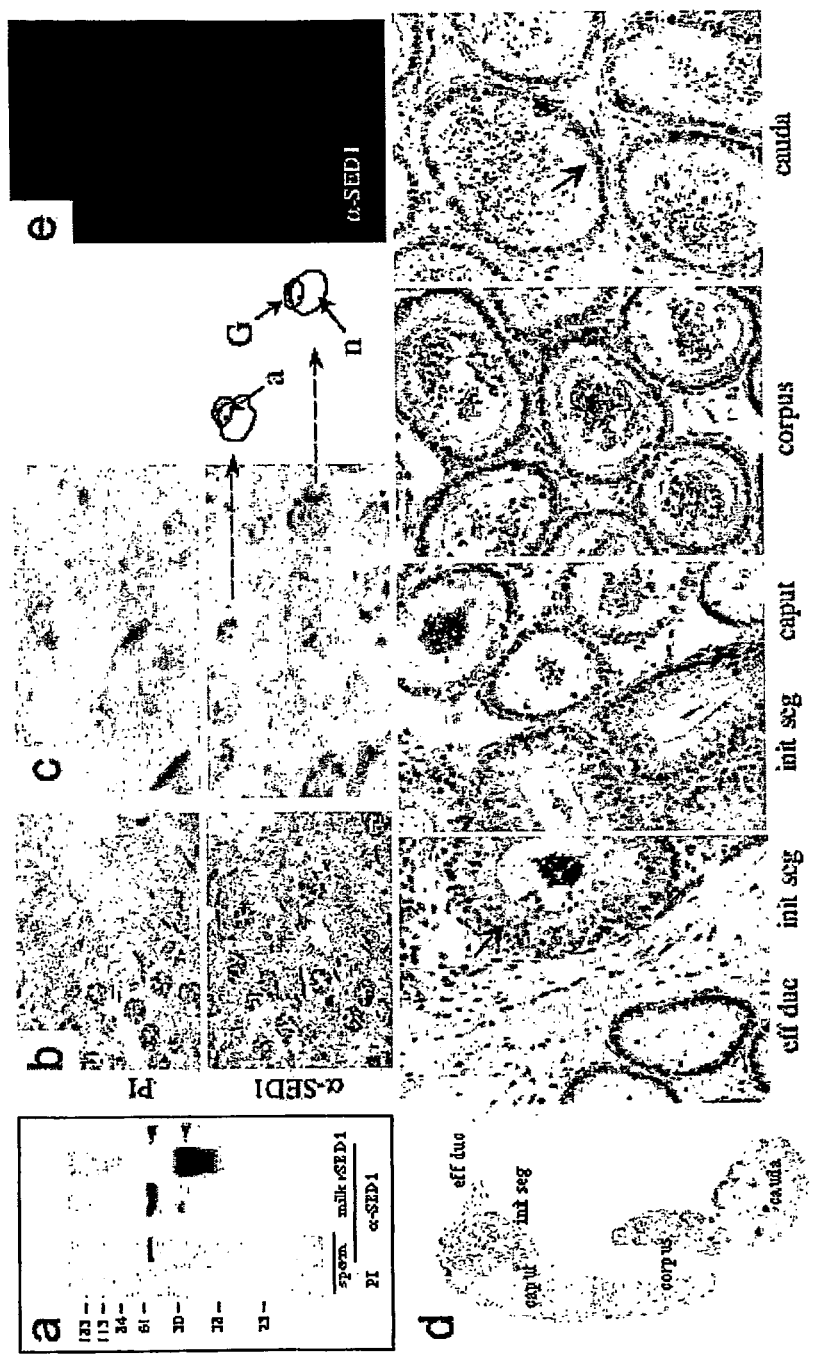
FIG. 1A is an immunoblot showing that SED1 is present in sperm.
FIG. 1B is a panel of micrographs showing SED1 is localized to the developing Golgi apparatus in differentiating spermatogenic cells.
FIG. 1C is a panel of micrographs showing Golgi (G) wraps around the clear vacuolar acrosome vesicle (a) containing a characteristic acrosomal granule, which is devoid of SED1 immunoreactivity.
FIG. 1D is a panel of micrographs of the epididymis prepared for anti-SED1 immunocytochemistry; the complete epididymis is represented in two noncontiguous pieces. SED1 immunoreactivity is abundantly expressed in the secretory principle cells (arrow) of the initial segment when sperm enter the epididymis, after which the epididymal epithelium is relatively negative for SED1.
FIG. 1E is a fluorescence micrograph showing SED1 is localized to the plasma membrane overlying the acrosome on the anterior sperm head as revealed by α-SED1 and FITC-conjugated goat-anti rabbit IgG.

It has been discovered that SED1 functions during mammalian fertilization. Mammalian fertilization was investigated using the mouse model. SED1 was cloned from mouse testis and denotes a secreted protein containing N-terminal Notch-like type II EGF repeats and C-terminal discoidin/F5/8 Complement domains (also referred to as discoidin C domains or discoidin/F5/F8 C domains). Murine SED1 is localized in the Golgi complex of differentiating spermatogenic cells, as well as in the initial segment of the caput epididymis, which together culminate in SED1 being tightly associated with a discrete domain of the sperm plasma membrane overlying the acrosome. Recombinant SED1 binds selectively to the zona pellucida of unfertilized oocytes, and competition assays with recombinant SED1, various SED1 domain constructs, and anti-SED1 antibodies indicate that SED1 participates in sperm-egg adhesion. SED1 null males show greatly reduced fertility in vivo, and their sperm are unable to bind to the egg zona pellucida in vitro without apparent effects on sperm morphology, number, acrosomal status, or motility. The various embodiments of the disclosure will be discussed in more detail below.

Prior to describing the various embodiments, the following definitions are provided and should be used unless otherwise indicated.

Definitions:

The term "organism" or "host" refers to any living entity comprised of at least one cell. A living organism can be as simple as, for example, a single eukaryotic cell or as complex as a mammal, including a human being.

The term "gamete adhesion modulator" refers to a compound that interferes with or promotes the adhesion of a male gamete to a female gamete. A gamete adhesion modulator includes, but is not limited to, polypeptides, small molecules, organic molecules, heterocyclic compounds, aromatic compounds, and the like. An exemplary gamete adhesion modulator includes, but is not limited to, SED1 polypeptides and polypeptides comprising at least one discoidin/C domain. "Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or a pharmaceutically acceptable salts thereof, with other chemical components, such as physiologically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "prodrug" refers to an agent, including nucleic acids and proteins, which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. 1. Lee and E. M. Topp, Eds., Transport Processes in Pharmaceutical Systems, Marcell Dekker, p.185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), C1 in. Neuropharmacol. 20(1): 1-12; Bundgaard (1979). Bioreversible derivatization of drugs-principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-30; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, MPS PharmSci., 2(1): E6; Sadzuka Y. (2000). Effective prodrug liposome and conversion to active metabolite, Curr Drug Metab., 1(1):3148; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "nucleic acid" is a term of art that refers to a string of at least two base-sugar-phosphate combinations. For naked DNA delivery, a polynucleotide contains more than 120 monomeric units since it must be distinguished from an oligonucleotide. However, for purposes of delivering RNA, RNAi and siRNA, either single or double stranded, a polynucleotide contains 2 or more monomeric units. Nucleotides are the monomeric units of nucleic acid polymers. The term includes deoxyribonucleic acid (DNA) and ribonucleic acid (RNA). RNA may be in the form of an tRNA (transfer RNA), snRNA (small nuclear RNA), rRNA (ribosomal RNA), mRNA (messenger RNA), anti-sense RNA, RNAi, siRNA, and ribozymes. The term also includes PNAs (peptide nucleic acids), phosphorothioates, and other variants of the phosphate backbone of native nucleic acids. Anti-sense is a polynucleotide that interferes with the function of DNA and/or RNA. Natural nucleic acids have a phosphate backbone, artificial nucleic acids may contain other types of backbones, but contain the same bases.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, 1), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gin: Asn), (Glu: Asp), (Gly: Ala), (His: Asn, Gln), (lle: Leu, Val), (Leu: lle, Val), (Lys: Arg), (Met: Leu, Tyr), (Ser: Thr), (Thr: Ser), (Tip: Tyr), (Tyr: Trp, Phe), and (Val: lle, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "dentity" and "similarity" can be readily calculated by known methods, including, but not limited to, those described in (Lesk, A. M., Ed. (1988) Computational Molecular Biology, Oxford University Press, New York; Smith, D. W., Ed. (1993) Biocomputing: Infomatics and Genome Projects. Academic Press, New York; Griffin, A. M., and Griffin, H. G., Eds. (1994) Computer Analysis of Sequence Data: Part I, Humana Press, New Jersey; von Heinje, G. (1987) Sequence Analysis in Molecular Biology, Academic Press; Gribskov, M. and Devereux, J., Eds. (1991) Sequence Analysis Primer. M Stockton Press, New York; Carillo, H. and Lipman, D. (1988) SIAM J Applied Math., 48,1073).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, ((1970) J. Mol. Biol., 48,443–453) algorithm (e.g., NBLAST, and XBLAST).

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating said symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "vector" is used in reference to a vehicle used to introduce a nucleic acid sequence into a cell. A viral vector is virus that has been modified to allow recombinant DNA sequences to be introduced into host cells or cell organelles.

The term "heterologous" means derived from a separate genetic source, a separate organism, or a separate species. Thus, a heterologous antigen is an antigen from a first genetic source expressed by a second genetic source. The second genetic source is typically a vector.

The term "antigen" means any substance that elicits an immune response in an organism. The immune response can be cellular, humoral, or a combination thereof. An antigen can have more than one epitope.

The term "epitope" means a particular site of a molecule to which an antibody binds.

The term "recombinant" generally refers to a non-naturally occurring nucleic acid, nucleic acid construct, or polypeptide. Such non-naturally occurring nucleic acids include combinations of DNA molecules of different origin that are joined using molecular biology technologies, or natural nucleic acids that have been modified, for example that have deletions, substitutions, inversions, insertions, etc. Recombinant also refers to the polypeptide encoded by the recombinant nucleic acid. Non-naturally occurring nucleic acids or polypeptides include nucleic acids and polypeptides modified by man.

The term "null mutation" means a mutation or change in a gene that results in the gene not being transcribed into RNA and/or translated into a functional protein product. Null mutations include, but are not limited to deletions, insertions, point mutations, transpositions, inversions, and substitutions.

Having defined some of the terms herein, the various embodiments of the disclosure will be described.

Compositions

One embodiment provides a composition, for example a pharmaceutical composition including a gamete adhesion modulator, for example a polypeptide including at least one discoidin/C domain in an amount effective to modulate mammalian gamete adhesion. The polypeptide can also include at least one EGF domain. Generally, the gamete adhesion modulator can interfere with SED1 binding of gametes or promote the binding of SED1 to gametes. The composition can optionally include a pharmaceutically acceptable carrier or excipient. Other suitable gamete adhesion modulators include small molecules such as organic compounds that interfere or promote SED1-mediated gamete adhesion, for example small molecules that mimic SED1 protein structure/function domains such as discoidin C domains.

In a particular embodiment, the gamete adhesion modulator competitively inhibits in vivo or in vitro binding of sperm to unfertilized zona pellucida. Alternatively, the gamete adhesion modulator promotes in vivo or in vitro binding of sperm to unfertilized zona pellucida. The gamete adhesion promoter can act directly on a gamete, SED1, or indirectly. In certain other embodiments, the gamete adhesion modulator includes SED1 polypeptide or a fragment thereof (SEQ ID NOs. 2-7).

Still another embodiment provides a recombinant polypeptide including SEQ ID Nos. 2-7 or a fragment thereof, wherein the recombinant polypeptide modulates mammalian gamete adhesion.

Another embodiment provides a non-human animal model including a homozygous null mutation in an endogenous nucleic acid sequence encoding SED1 (SEQ ID NO. 2) or a fragment thereof. Generally, the non-human animal model is a transgenic mouse engineered so that it does not express functional SED1. The gametes of the transgenic mouse can be isolated and used for example in assays for identifying other modulators of gamete adhesion.

Yet another embodiment provides an isolated antibody that selectively binds to at least one epitope of SED1 (SEQ ID NO. 2) or a fragment thereof, and modulates mammalian gamete adhesion. The antibody can be polyclonal, monoclonal, single chained, chimeric, humanized, or a fragment thereof.

Methods

Other embodiments provide methods of modulating mammalian gamete adhesion. One exemplary method provides administering to a mammal an amount of a gamete adhesion modulator sufficient to modulate SED1-mediated gamete adhesion.

Another method provides combining mammalian sperm and a mammalian unfertilized oocyte in the presence of an amount of a polypeptide effective to modulate gamete adhesion, wherein the polypeptide includes at least on discoidin/C domain. The polypeptide optionally includes at least one EGF domain. In practice, the polypeptide competitively inhibits in vivo or in vitro binding of sperm to unfertilized zona pellucida or promotes in vivo or in vitro binding of sperm to unfertilized zona pellucida. A representative polypeptide includes, but is not limited to, SED1 polypeptide or a fragment thereof and SEQ ID NOs. 2-7 or a fragment thereof.

Still another embodiment provides a method for diagnosing infertility. An exemplary method for diagnosing infertility includes detecting SED1 polypeptide, or a homolog thereof, on a mammalian male gamete and comparing the level of detected SED1 on the mammalian male gamete with a predetermined level of SED1 indicative of a fertile mammalian male gamete. A level of detected SED1 on the male gamete lower than the predetermined level of SED1 is indicative of infertility. For example, an antibody can be used to detect the SED1 polypeptide or homolog thereof. The antibody can be attached to a solid support including, but not limited to, a dip stick, array surface, polymer, metal, pin, comb, and a multi-well plate.

Another embodiment for diagnosing infertility includes using nucleic sequence variations in SED1 as a biomarker for infertility, for example male infertility. An exemplary method includes assaying a sample from a male host for a nucleic acid sequence variation in a gene or transcript encoding or believed to encode SED1 or a homolog thereof. In this embodiment, a nucleic acid variation can be determined by comparing detected SED1 nucleic acid sequences or fragments thereof to predetermined nucleic acid sequences known to encode a functional SED1 polypeptide. The presence of a nucleic acid sequence variation in the gene or transcript is an indicator of infertility and be the basis for a diagnosis of infertility.

In some embodiments, the nucleic acid sequence variation includes, but is not limited to, a deletion, insertion, inversion, transposition, single nucleotide polymorphism, a substitution, or combinations thereof. Such variations can be detected using probes that hybridize to specific portions of SED1, for example SEQ ID No. 1 or fragments thereof. The probes can be used in primer extension reactions. Primer extension reaction products having more or less nucleotides than primer extension products formed from a sequence known to encode functional SED1 can indicate a nucleic acid sequence variation indicative of infertility. Methods for detecting sequence variations of specific nucleic acid sequences are known in the art and are within the scope of this disclosure.

Yet another embodiment provides a contraceptive method. A representative contraceptive method includes contacting a mammalian gamete with a compound that competitively interferes with SED1-mediated gamete adhesion. The compound can be a polypeptide, for example SED1 polypeptide (SEQ ID NOS. 2-7) or an antibody specific for SED1 polypeptides. Generally, the compound includes a polypeptide comprising at least one discoidin/C domain and optionally comprises at least one EGF domain.

Still another embodiment provides a method for increasing gamete adhesion. This embodiment provides contacting a male mammalian gamete with a polypeptide comprising SEQ ID No 2 or 3 or a fragment thereof in an amount sufficient to promote adhesion between the male mammalian gamete and a female mammalian gamete.

Another embodiment provides a method for modulating male fertility comprising administering a gamete adhesion modulator to a male host in an amount effective to modulate SED1 expression or biological activity, for example SED1 association with male gametes. The gamete adhesion modulator can, for example, reduce the expression of SED1 by spermatogenic cells and thereby reduce the level of SED1 associated with a male host's gametes.

Still other compositions including a gamete adhesion modulator can be used as a contraceptive, for example a topical or oral contraceptive. Topical contraceptive compositions can be applied vaginally, for example in the form of a suppository, cream, gel, solution, colloid etc. Alternatively a composition including a gamete adhesion modulator can be applied to a contraceptive device.

Screening,

The disclosure also provides methods for identifying gamete adhesion modulators. As used herein the term "test compound" or "modulator" refers to any molecule that may potentially inhibit or enhance SED1 mediated mammalian gamete adhesion, in particular binding of male gametes to zona pellucida of unfertilized oocytes. Representative modulators mimic or increase activity or expression of SED1 or inhibit the activity of SED1. The test compound or modulator can be a protein or fragment thereof, a small molecule, or even a nucleic acid molecule. Some test compounds and modulators can be compounds that are structurally related to SED1 polypeptides. Using lead compounds to help develop improved compounds is known as "rational drug design" and includes not only comparisons with known inhibitors and activators, but predictions relating to the structure of target molecules.

One embodiment provides a method for identifying modulators of gamete adhesion including assaying binding of SED1 polypeptide, a homolog, or fragment thereof to zona pellucida of unfertilized oocyte or a fragment thereof in the presence of a test compound, and selecting the test compound that promotes or interferes with SED1 binding to zona pellucida of unfertilized oocyte and promotes or interferes with gamete adhesion compared to a control compound.

Another embodiment provides a method for identifying modulators of gamete adhesion comprising assaying binding of SED1 polypeptide, a homolog, or fragment thereof to ZP2, ZP3, or both ZP2 and ZP3 or a fragment thereof in the presence of a test compound, and selecting the test compound that promotes or interferes with SED1 binding to ZP2, ZP3, or both ZP2 and ZP3 and promotes or interferes with gamete adhesion compared to a control compound.

In another embodiment, small molecule libraries that are believed to meet the basic criteria for useful drugs can be screened to identify useful compounds. Screening of such libraries, including combinatorially generated libraries (e.g., expression libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Test compounds may include fragments or parts of naturally-occurring compounds, or may be found as active combinations of known compounds, which are otherwise inactive. Compounds isolated from natural sources, such as animals, bacteria, fungi, plant sources, including leaves and bark, and marine samples can be assayed as candidates for the presence of potentially useful pharmaceutical agents. It will be understood that the pharmaceutical agents to be screened could also be derived or synthesized from chemical compositions or man-made compounds. Thus, it is understood that the test compound identified by embodiments of the present disclosure may be peptide, polypeptide, polynucleotide, small molecule inhibitors, small molecule inducers, organic or inorganic, or any other compounds that may be designed based on known inhibitors or stimulators.

Other suitable modulators include antisense molecules, catalytic nucleic acids such as ribozymes, and antibodies (including single chain antibodies), each of which would be specific for SED1. For example, an antisense molecule that binds to a translational or transcriptional start site, or splice junctions, are within the scope of a test compound.

In addition to the modulating compounds initially identified, other sterically similar compounds may be formulated to mimic the key portions of the structure of the modulators, for example discoidin/C domains. Such compounds, which may include peptidomimetics of peptide modulators, may be used in the same manner as the initial modulators.

An inhibitor or activator according to the present disclosure may be one which exerts its inhibitory or activating effect upstream, downstream, directly, or indirectly on SED1 mediated gamete adhesion. In one embodiment, the inhibition or activation by an identified modulator results in the modulation of SED1 biological activity or expression as compared to that observed in the absence of the added test compound.

Screening for Modulators of Gamete Adhesion

Embodiments of the present disclosure include methods for identifying modulators of the function, expression, or bioavailability of SED1, in particular the function of SED1 in gamete adhesion. The modulator may modulate gamete adhesion, for example SED1-mediated gamete adhesion, directly or indirectly. Direct modulation refers to a physical interaction between the modulator and SED1, a SED1 receptor, or a SED1 binding site, for example binding of the modulator to a region of the SED1. Indirect modulation of SED1-mediated gamete adhesion can be accomplished when the modulator physically associates with a cofactor, second protein or second biological molecule that interacts with SED1 or a gamete either directly or indirectly. Additionally, indirect modulation would include modulators that affect the expression or the translation of RNA encoding SED1.

In some embodiments, the assays can include random screening of large libraries of test compounds. Alternatively, the assays may be used to focus on particular classes of compounds suspected of modulating the function or expression of SED1 in reproductive tissue as a result of the classes of compounds containing a specific structure or motif.

Assays can include determinations of SED1 expression, protein expression, protein activity, or binding activity. Other assays can include determinations of nucleic acid transcription or translation, for example mRNA levels, mRNA stability, mRNA degradation, transcription rates, and translation rates.

In one embodiment, the identification of a gamete adhesion modulator is based on the function of SED1 in the presence and absence of a test compound. The test compound or modulator can be any substance that alters or is believed to alter the function of SED1, in particular the function of SED1 in gamete adhesion. Typically, a modulator will be selected that reduces, eliminates, or mitigates SED1 mediated gamete adhesion.

One exemplary method includes contacting SED1 with at least a first test compound, and assaying for an interaction between SED1 and the first test compound with an assay. The assaying can include determining SED1-mediated gamete adhesion.

Specific assay endpoints or interactions that may be measured in the disclosed embodiments include, but are not limited to, assaying for fertilization, gamete adhesion, SED1 down regulation or turnover. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms including transgenic animals.

Other screening methods include using labeled SED1 to identify a test compound. SED1 can be labeled using standard labeling procedures that are well known and used in the art. Such labels include, but are not limited to, radioactive, fluorescent, biological and enzymatic tags.

Another embodiment provides a method for identifying a modulator of SED1 expression by determining the effect a test compound has on the expression of SED1 in reproductive tissue cells such as spermatogenic cells. For example spermatogenic cells expressing SED1 can be contacted with a test compound. SED1 expression can be determined by detecting SED1 protein expression or SED1 mRNA transcription or translation. Suitable cells for this assay include, but are not limited to, immortalized cell lines, primary cell culture, or cells engineered to express SED1. Compounds that modulate the expression of SED1, in particular that decrease the expression or bioavailability of SED1, can be selected as contraceptive agents. Compounds that modulate the expression of SED1, in particular that increase the expression or bioavailability of SED1, can be used as therapeutic agents for the treatment of infertility.

Phage Display

One embodiment for identifying modulators of SED1 includes using phage display technology to identify polypeptides that specifically bind to SED1 and do not substantially bind to other polypeptides. Phage technology uses bacteriophages, viruses that contain single stranded DNA within a protein cylinder. Within the genome of the bacteriophage (pIII or pVIII regions usually), DNA sequences that encode for various peptides can be inserted. These inserted sequences encode for peptides that are displayed on the capsid (or outer cylinder) of the bacteriophage. Thus, bacteriophage libraries contain bacteriophages of great diversity in their ligand structure. Depending on the length and complexity of the peptide attached to the bacteriophage, libraries can contain billions of different peptide structures and thus billions of unique bacteriophages.

Phage display technology can be used to find a masking ligand against SED1 or SED1 binding sites. Generally, the method starts by fixing SED1 to a substrate, for example sepharose beads that have terminal amino groups can be used. With a common crosslinking strategy, the amine structure on the beads will attach to a carboxyl group on SED1.

After it is verified that SED1 is attached to the sepharose beads through the use of a sulfate group assay, phage libraries will be mixed with the beads. Those bacteriophage that possess ligands with an affinity for SED1 will bind to the SED1/sepharose bead complex. Those that do not will be washed away. The phage that are bound to the bead complex are then eluted using various buffers.

Once eluted, phage with affinity for SED1 will then be introduced to a K91 bacteria strain. The viruses will then infect these bacteria and insert their DNA into the host's DNA, thereby using the bacteria to make more bacteriophage.

The amplified bacteriophage contain populations that are more concentrated with ligands of higher affinity for SED1. The phage can be harvested from the bacteria cultures and then passed again through a SED1/sepharose bead complex for further purification. Typically, there are three purification steps (where phage will be introduced to beads with SED1 and phage will be amplified using bacteria hosts).

After purification of phage, the ligands on these purified species can be sequenced using an independent laboratory. Once sequenced, affinity of these ligands will be verified using a SED1-ligand assay.

Once it is established that the ligand binds to SED1, the ligand can be tested using in vitro culture techniques. SED1 can be plated on culture plates, and gametes can be introduced to such plates with or without application of the ligand with affinity to SED1. If the ligand masks SED1, reduced gamete adhesion can be detected.

In vitro Assays

Another embodiment provides for in vitro assays for the identification of SED1 modulators. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule, for example a nucleic acid encoding SED1, in a specific fashion is strong evidence of a related biological effect. Such a molecule can bind to a SED1 nucleic acid and modulate expression of SED1, for example upregulate expression of SED1. The binding of a molecule to a target may, in and of itself, be inhibitory, due to steric, allosteric or charge—charge interactions or may downregulate or inactivate SED1. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

Cell Assays

Other embodiments include methods of screening compounds for their ability to modulate SED1 in cells. Various cell lines can be utilized for such screening assays, including cells specifically engineered for this purpose. Suitable cells include, but are not limited to, mammalian spermatogenic cells or reproductive tissue can be used. Cells can also be engineered to express SED1 or a modulator of SED1 or a combination of both SED1 or a modulator of SED1. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The introduction of DNA into a cell or a host cell is well known technology in the field of molecular biology and is described, for example, in Sambrook et al., Molecular Cloning 3rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with the disclosed expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE, La Jolla, Calif.). Alternatively, bacterial cells such as E. coli LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include, but are not limited to, YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In vivo Assays

In vivo assays involve the use of various animal models, including non-human transgenic animals that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species. In such assays, one or more test compounds are administered to an animal, and the ability of the test compound(s) to alter one or more characteristics, as compared to a similar animal not treated with the test compound(s), identifies a modulator. The characteristics may be any of those discussed above with regard to the function of a particular compound (e.g., enzyme, receptor, hormone) or cell (e.g., growth or regeneration), or instead a broader indication nerve cell regeneration, axonal growth or regeneration, or the like.

Other embodiments provide methods of screening for a test compound that modulates the function of SED1. In these embodiments, a representative method generally includes the steps of administering a test compound to the animal and determining the ability of the test compound to reduce one or more characteristics of gamete adhesion and/or fertilization.

Treatment of these animals with test compounds will involve the administration of the compound, in an appropriate form, to the animal. Administration will be by any route that could be utilized for clinical or non-clinical purposes, including, but not limited to, oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

Expression Systems

Some embodiments of the present disclosure provided compositions containing gamete adhesion modulators that can be expressed as encoded polypeptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic and amino sequences.

Generally speaking, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the present disclosure does not exclude the possibility of employing a genomic version of a particular gene where desired.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinanty introduced exogenous DNA segment or gene. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded polypeptide protease or proteinase inhibitor in accordance with the present disclosure one would prepare an expression vector that includes a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli$_X$*1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051, incorporated herein by reference).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the Bg/I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk$^-$, hgprt$^-$ or aprt$^-$ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

It is contemplated that the isolated nucleic acids of the disclosure may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

Purification of Expressed Proteins

Further aspects of the present disclosure concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., Biochem. Biophys. Res. Comm., 76:425, 1977). It will therefore be appreciated that under differing electrophoresis conditions, the apparent molecular weights of purified or partially purified expression products may vary.

Pharmaceutical Compositions

Pharmaceutical compositions and dosage forms of the disclosure include a pharmaceutically acceptable salt of disclosed compositions or compounds or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. A parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure include a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Topical dosage forms of the disclosure include, but are not limited to, creams, lotions, ointments, gels, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos.: 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of an gamete adhesion modulator of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery.

Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a gamete adhesion modulator can be used to further adjust the properties of the resulting composition.

EXPERIMENTAL PROCEDURES

Cloning and Expression of Mouse SED1

Murine SED1 cDNA was cloned from testis RNA by RT-PCR using primers based upon published data (Ensslin et al., 1998). SED1 and truncated forms of SED1 were expressed in E. coli with an N-terminal $(His)_6$-tag (Invitrogen). Cell were lysed, insoluble material solubilized in resolving buffer (8 M urea, 30 mM phosphate, 50 mM Tris-HCI [pH 8.1], and 5 mM imidazole), and subjected to affinity chromatography on $Ni^{2+}$-Sepharose (Invitrogen). Recombinant protein was selectively eluted from the column using resolving buffer supplemented with 250 mM imidazole and renatured by repetitive dialysis against PBS supplemented with 0.3 mM DTT.

Full-length SED1 with a N-terminal GST tag was constructed using the pMelBac baculovirus transfer vector (Invitrogen). Upon cotransfection with Bac-N-Blue DNA (Invitrogen), viral DNA containing SED1 was isolated, and high-titer viral stocks were produced. High five cells were infected and incubated for 65 hr at 27° C., and the cell supernatant was assayed for SED1 expression by Western blotting. For GST-SED1 purification, the cell supernatant was adjusted to pH 7.4 and 1 M urea (final concentration) with subsequent addition of glutathione-Sepharose (Pharmacia). GST-SED1 was eluted from glutathione-Sepharose using 100 mM phosphate (pH 8.6), 50 mM glutathione, 1 M urea, and 1 mM DTT, followed by extensive dialysis in PBS with 0.3 mM DTT.

For expression in COS-7 cells, SED1 was amplified by RT-PCR and cloned into the pcDNA3.1 DN5-His-Topo mammalian expression vector (Invitrogen). COS-7 cells were transfected with FuGENE (Roche) in serum-free DMEM according to the manufacturer's protocol. SED1 enriched membrane vesicles secreted into the culture media were purified using differential centrifugation (Oshima et al., 2002).

Recombinant SED1 and truncated forms of SED1 were biotinylated using EZ-Link Sulfo-NHS-LC-LC-Biotin (Pierce) according to the manufacturer's protocol.

Antibody Production and Western Blot Analysis

Affinity-purified $(His)_6$-tagged SED1 was subjected to preparative SDS-PAGE. The gel was stained with 100 mM KCl at 0° C. (Nelles and Bamburg, 1976), and the band representing SED1 was removed and served as antigen for the immunization of rabbits and chickens. Reactivity of preimmune and immune sera was determined using ELISA. Purification of anti-SED1 IgG was performed using an IgG Purification Kit (Pierce).

For Western blot analysis, cauda epididymal sperm were washed, pelleted, solubilized in 8 M urea, and the soluble sperm proteins collected after centrifugation. SED1-expressing SF9 cells were washed free of medium, sonicated ,and centrifuged to remove insoluble material. Mouse milk was directly solubilized in sample buffer. In all instances, soluble proteins were resolved on 10% polyacrylamide gels and transferred onto lmmobilon-P membranes (Millipore). The membranes were blocked in TBST (150 mM NaCI, 50 mM Tris/HCI [pH 7.5], and 0.1% Tween 20) containing 2% BSA for one hour at 25° C. After incubation with anti-SED1 or anti-GalT I (Youakim et al., 1994) antibody and rinsing, the bound IgG was detected with goat anti-rabbit-HRP (Amersham) and developed using ECL+plus (Amersham). Protein loading was assayed by probing blots with monoclonal antibodies against α-tubulin (Sigma: clone B-5-1-2).

Immunohistochemistry

Testis and epididymis were isolated from CD-1 mice, fixed overnight in Bouin's solution, and paraffin-embedded. Sections (4 μm) were subjected to microwave "antigen retrieval" for two times at 6 min full power with 1 min cooling period, in 10 mM sodium citrate (pH 6) (Janssen et al., 1994). Sections were cooled, blocked, and processed for immunocytochemistry using 1:100 primary antibody, 1:1,000 HRP-conjugated goat-anti-rabbit (Amersham), and "liquid DAB-black substrate kit" (Zymed).

Cauda epididymal sperm were collected in dmKBRT (Lu and Shur, 1997; Youakim et al., 1994), filtered (3-35/27 Nitex, Sefar America), washed three times in PBS, and mounted on polylysine-coated slides. Sperm were fixed at −20° C. in methanol for 10 min, rinsed, and blocked for 1 hr in PBS containing 5% normal goat serum (PBS/NGS). Slides were incubated with rabbit anti-SED1 sera (1:100 dilution) in PBS/NGS for 1 hr at 25° C., washed, and incubated with FITC labeled goat anti-rabbit antibodies (1:2,000) (Zymed) for 45 min at 25° C. After washing, the slides were mounted in PBS with 70% glycerol and examined under a Nikon E800 microscope. For analysis of live sperm, 100 μl of washed sperm ($5 \times 10^6$ sperm/ml) in PBS, 0.25% BSA were mixed with anti-serum against SED1, GalT I, or preimmune serum (1:50 final dilution) and incubated for 30 min at 25° C. The sperm suspension was washed free of excess antiserum by layering onto 1 ml of PBS, 3% BSA, and centrifuged at 600× g for 5 min at 25° C. The sperm suspension was mixed with Fab fragments of goat anti-rabbit (1:1000 final, Alexa Fluor 594, Molecular Probes), or goat anti-rabbit-FITC (Zymed), for 30 min at 25° C. in the dark, and washed as described above. The sperm were fixed in 1% paraformaldehyde for 10 min and viewed under a Nikon E800 microscope. Controls were prepared by substituting the primary antibody with preimmune serum and nonspecific rabbit IgGs.

Sperm Capacitation and Binding to the Egg Coat

Sperm capacitation and egg binding assays were performed as previously reported (Lu and Shur, 1997). For analysis of acrosomal status, capacitated sperm were fixed in 2% paraformaldehyde, stained with Coomassie, and viewed under the microscope as described (Larson and Miller, 1999). To induce the acrosome reaction, A23187 (10 μM final, Sigma) was added to capacitated sperm and incubated an additional 10 min before fixation and Coomassie staining. For egg binding assays, eggs from 8-week-old superovulated females were freed from their cumulus cells by hyaluronidase treatment (0.2%, 10 min, 25° C.), washed in dmKBRT, and added in groups of 20 eggs to 40 μl drops dmKBRT supplemented with competing agents under paraffin oil. Three to five two-cell embryos flushed from oviducts of superovulated females were included in every drop as negative controls. 10 μl sperm solution was added to the egg-containing drops and binding was allowed to proceed for 30 min at 37° C. Afterwards, sperm-egg complexes were washed free of unbound or loosely bound sperm. Washing was stopped when <3 sperm remained bound to two-cell embryos. Sperm-egg complexes were fixed in 4% formaldehyde, and the number of sperm attached to the egg zona pellucida was determined.

Binding of SED1-Coated Microspheres to Zona Pellucida and Sperm

NeutrAvidin-labeled fluorescent beads (Fluo-Spheres, Molecular Probes), 1 μm, were coated with biotinylated SED1 proteins as described by the manufacturer. WGA-biotin served as a positive control protein; UEAI-biotin, BSA-biotin, cytochrome C-biotin, and uncoupled Fluo-Spheres were used as negative controls (Aviles et al., 1997). Ovulated oocytes, two-cell embryos, and zona pellucida from ovarian oocytes were isolated as described and combined into 40 μl droplets of dmKBRT. To these droplets, 5-10 μl of protein-coated Fluo-Spheres were added and incubated for 1 hr at 25° C. The suspension was washed with a microbore pipette to remove unbound Fluo-Spheres and subsequently examined under the microscope.

For analysis of SED1 binding to sperm, cauda epididymal sperm was collected in dmKBRT buffer, filtered and washed twice (400× g, 5 min), and adjusted to $10^3$ sperm/μl. To 50 μl sperm suspension, 3 μl of SED1-coated Fluo-Spheres (0.2 μm) and 7 μl of either GRGDNP-peptide (Biomol) or GRADSP control peptide (Buckley et al., 1999) was added, final concentration 0-10 mM, and incubated for 30 min at 25° C. Sperm were washed twice in dmKBRT buffer to remove unbound Fluo-Spheres, mounted, and examined under the microscope.

Purification of Zona Pellucida Glycoproteins for SED1 Blot Overlay Analysis

The purification of zona pellucida glycoproteins was done as published elsewhere (Miller et al., 1992). The proteins were resolved on 10% polyacrylamide gels and transferred onto Immobilon-P membranes (Millipore) as above. The membranes were blocked in TBST containing 2% BSA for 1 hr at 25° C. Subsequently, membranes were incubated with either $(His)_6$-SED1, biotinylated $(His)_6$-SED1, SED1 prepared from COS-7 cells, or biotinylated WGA-lectin (positive control) for 1 hr at 25° C. and washed three times for 10 min in TBST, followed by incubation with either rabbit anti-SED1 and goat anti-rabbit-HRP, or Streptavidin-HRP (Zymed). The membranes were washed, developed, and exposed to film as above.

Creation of SED1 Null Mice

Two BAG clones were identified that contained the SED1 gene by screening a commercial 129/Sv ES cell mouse BAG library (Genome Systems) with PCR primers corresponding to exon 2 and exon 3. A 9 kb EcoRI fragment containing the SED1 coding region was subcloned into the bluescript vector KS+(FIG. 4A). The first loxP site, as well as the neo cassette and two frt sites, were inserted 140 bp upstream of the ATG start signal, leaving 1.45 kb of 5'sequences. The second loxP site was inserted 160 bp downstream of the signal peptide. At the 3'end, the target vector was shortened by 1.5 kb. An additional EcoRI site was introduced into the SED1 gene to create diagnostic restriction sites for identifying the targeted allele (FIG. 4A).

The target vector (TVSED1) was linearized and transfected into ES cells. DNA from neomycin-resistant clones was subjected to a restriction digest with EcoRI, separated on an 0.8% agarose gel, blotted onto a nylon membrane, and probed for an homologous recombination event using $^{32}$P-dCTP-labeled probes either internal to the region of homology (372 bp Internal Probe) or external (335 bp External Probe) to the targeting construct (FIG. 4B). but of 288 neomycin-resistant ES clones, 13 (4.2%) could be identified as positive for the targeted SED1 allele.

Two independent parental clones positive for the SED7-targeted allele (#164, #262) were transfected with Cre recombinase to excise the neo-selection cassette and the exon containing the signal peptide. The genotype of the ES clones was confirmed by PCR analysis using primers that amplify either a 517 bp fragment from the wild-type allele or a 222 bp fragment from the targeted allele (forward, 5'-CCTCAG-GCTGAGGACTGGCAGCGGC (SEQ ID NO. 8); reverse, 5'-GCTGTCAC CGGGTGTCCAGGGTCACC (SEQ ID NO. 9)) (FIG. 4A). Four ES cell clones were expanded and injected into blastocysts, which were transferred into pseudopregnant females. The blastocyst injections resulted in nine highly chimeric mice, assayed by coat color. The presence of the mutated SED1 allele was confirmed in two mice from each of the original parental clones. Chimeras were mated to C57Bl/6 wild-type females to create founder mice heterozygous for the SED1 mutation. Homozygous SED1 null mice were created by heterozygous matings. Genotypes of the resulting mice were determined using the same PCR strategy as used for genotyping ES clones (FIG. 4C).

EXAMPLES

Example 1

Production of Recombinant SED1 and Anti-SED1 Antibodies

Mouse SED1 was cloned from a testis library (EMBL accession number Y11684). The deduced 426 amino acid (aa) open reading frame encodes an N-terminal 22 aa cleavable signal sequence peptide, two Notch-like type 11 EGF repeats (the second of which contains an RGD motif, and two C-terminal discoidin/C domains (see FIG. 2C insert). Recombinant SED1 was expressed in $E.\ coli$ as a $(His)_6$-fusion protein, purified, and used to immunize rabbits and chickens. The resulting anti-SED1 antibodies recognize a single band of ~58 kDa in sperm and testis lysates (not shown), similar to that seen in mouse milk, which is a rich source of the SED1 homolog MFG-E8 (Stubbs et al., 1990) (FIG. 1A). Preimmune sera failed to produce any reaction. SED1 expressed in insect cells migrated as expected for the partially glycosylated recombinant protein.

Example 2

Immunocytochemical Localization of SED1 in the Male Genital Tract

SED1 immunoreactivity localizes to the Golgi apparatus of developing spermatogenic cells (FIGS. 1B and 1C). SED1 immunoreactivity could be attributed to the Golgi, as opposed to the developing acrosome, due to the characteristic morphology of the Golgi that wraps around the developing acrosomal vesicle. The acrosome has a characteristic clear vacuolar appearance containing the acrosomal granule and is devoid of SED1 immunoreactivity. The localization of SED1 to the Golgi suggests that it is secreted to the sperm surface, consistent with the presence of a cleavable signal sequence peptide (Stubbs et al., 1990). There is some SED1 immunoreactivity in what appears to be Sertoli cells, as well as some interstitial cells between the seminiferous tubules (not shown), the functional significance of which is unclear. Parallel studies using antibodies isolated from rabbit serum or chicken eggs produced similar immuno-localization (not shown). Preimmune rabbit (or chicken) immunoglobulins produced only background levels of staining (FIG. 1A-D.

Example 3

Epididymal Immunolocalization

Sperm leave the testis through the efferent ductules and enter the initial segment of the caput epididymis. Here, they are exposed to SED1 secreted from the principle, or secretory, cells of the epididymal epithelium, which are the predominant immunoreactive cells of the male reproductive tract (FIG. 1D). Subsequent portions of the epididymal epithelium show low levels of immunoreactivity, although the sperm remain immunoreactive. As sperm exit the pididymis, SED1 immunoreactivity is high in clear cells of the cauda epididymis, which are responsible for absorption of excess secretion products (Robaire and Hermo, 1994). A lower level of immunoreactivity is found associated with the apical surface of the principle cells of the cauda epididymis. As above, chicken immunoglobulins produced similar localization (data not shown). These data suggest that SED1 is secreted into the lumen of the caput epididymis, where it coats sperm, and excess SED1 is removed by the clear cells of the cauda epididymis as sperm enter the vas deferens.

Example 4

SED1 Localization on the Sperm Surface

On washed, fixed cauda epididymal sperm, SED1 is restricted to the plasma membrane overlying the acrosome (FIG. 1E), the area of the sperm surface responsible for initial binding to the zona pellucida (Primakoff and Myles, 2002; Wassarman et al., 2001). Preimmune IgG produced only background levels of fluorescence (not shown). SED1 localization on the plasma membrane was confirmed by incubating live, unfixed sperm with anti-SED1 antiserum in suspension (see FIG. 6B).

Example 5

Anti-SED1 IgG and Recombinant SED1 Inhibit Sperm-Egg Binding

Figure 2:
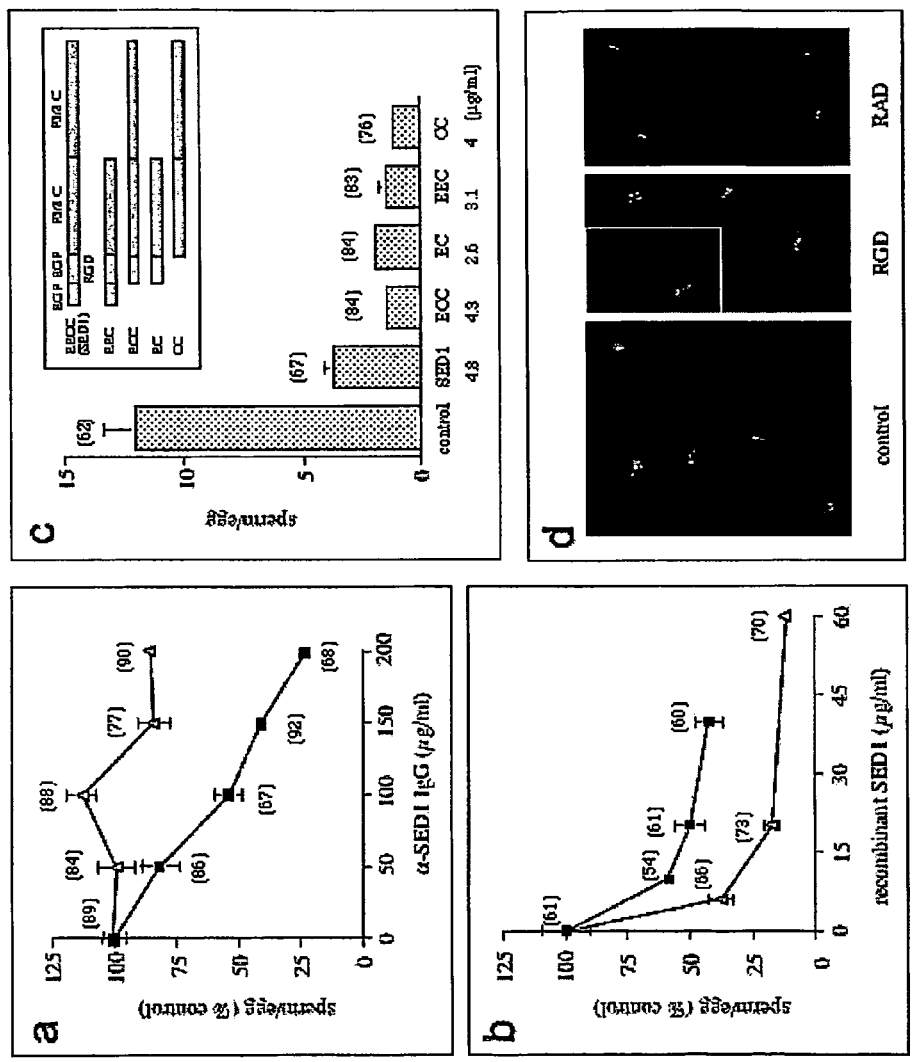
FIG. 2A is a line graph showing α-SED1 IgG inhibits sperm binding to the zona pellucida in a dose-dependent manner; at 200 µg/ml, sperm-zona binding is suppressed by 75%.
FIG. 2B is a line graph showing SED1 fusion proteins expressed in bacteria or insect cells competitively inhibit sperm binding to the zona pellucida in a dose-dependent manner.
FIG. 2C is a bar graph showing sperm binding to the zona pellucida is competitively inhibited by full-length (His)$_6$-SED1 fusion protein (SED1) and SED1 truncated fusion proteins that contain a discoidin/C domain.
FIG. 2D is a fluorescence micrograph showing fluorescent beads (0.2 μm) conjugated with SED1 bind to the dorsal anterior aspect of the sperm plasma membrane, similar to the distribution of endogenous SED1

The biological activity of SED1 was initially assessed by competitive sperm-egg binding assays. Purified anti-SED1 IgG produced a dose-dependent inhibition of sperm binding to the zona pellucida, relative to controls (FIG. 2A). Sperm motility appeared to be unaffected, even at concentrations of 200 μg/ml IgG, nor was there any evidence of antibody-mediated sperm agglutination that could account for the inhibition of sperm-egg binding. Preimmune IgG had no significant effect on sperm-egg binding at concentrations from 50-200 μg/ml. As expected, the original rabbit anti-SED1 antiserum also produced a dose-dependent inhibition of sperm-egg binding, whereas preimmune serum did not (not shown).

To determine if SED1 itself could inhibit sperm binding to the egg, recombinant SED1 was produced in two different expression systems, purified, and added individually to sperm-egg binding assays. Recombinant SED1, expressed either in bacteria as a $(His)_6$ fusion protein or in insect cells as a GST-fusion protein, competitively inhibited sperm binding to the egg coat in a dose-dependent manner (FIG. 2B). Pretreatment of either recombinant protein with Proteinase K destroyed its biological activity (not shown). The two recombinant proteins had similar biological activities when normalized for differences in their molecular weight (MW), suggesting that the N-terminal tags, i.e., GST and $(His)_6$, did not contribute to biological activity, nor did any post-translational processing.

Example 6

SED1 Function Requires a Discoidin/C Domain

The SED1 protein family has two distinct binding motifs that have been implicated in their adhesive function (Andersen et al., 1997, 2000; Fuentes-Prior et al., 2002; Penta et al., 1999). An RGD motif located within the second EGF domain has been suggested to mediate integrin-dependent binding to cells, whereas the discoidin/C domains are thought to bind negatively charged headgroups on membranes as well as to extracellular matrix components. To determine which, if either, of these domains is responsible for SED1 biological activity during gamete adhesion, different (His)6-fusion proteins were tested for activity in sperm-egg binding assays (FIG. 2C).

Intact $(His)_6$-SED1 containing both EGF repeats both discoidin/C domains (EECC) inhibited sperm-egg binding, as did truncated forms of SED1 (EEC, ECC, EC, CC). Furthermore, the intact and truncated SED1 proteins produced similar levels of inhibition, at constant molar ratios, as long as one discoidin/C domain was present (FIG. 2C). Thus, EGF domains are not required for competitive inhibition of sperm-egg binding, implicating the discoidin/C domains in mediating SED1 binding to gamete surfaces. This possibility is consistent with structural and biochemical data, indicating that the discoidin/C domains are able to bind a variety of molecular species, including phospholipid headgroups on membranes, such as on sperm, as well as carbohydrate epitopes in the extracellular matrix, as would be present in the zona pellucida (Fuentes-Prior et al., 2002; Macedo-Ribeiro et al., 1999; Pratt et al., 1999).

Although the above results suggest that the EGF domains do not contribute to competitive inhibition of sperm-egg binding, the ability of RGD peptide to competitively inhibit the binding of SED1 to sperm was directly tested. Recombinant SED1 was conjugated to 0.2 μm fluorescent beads and added to sperm isolated from the caput and cauda (±capacitation) epididymis. RAD peptide was used as control (Buckley et al., 1999). In no instance did RGD peptide produce any specific inhibition of SED1 binding to sperm when assayed at 1-10 mM (FIG. 2D). Repeated attempts to express the EGF domains as truncated recombinant proteins (EE) failed despite being cloned into three different fusion constructs (i.e., $[His]_6$-EE, GST-EE and Thioredoxin-EE). Nevertheless, the inability of RGD to affect SED1 binding to sperm is consistent with SED1 biological activity residing within the discoidin/C domains, rather than within the EGF repeats.

Example 7

SED1 Binding to the Zona Pellucida

The results from competitive inhibition assays above are consistent with SED1 participation in sperm-egg binding and implicate the discoidin/C domains in mediating SED1 attachment to gametes. Direct binding of full-length SED1, as well as SED1 truncated proteins, to the zona pellucida was investigated by assaying (1) the binding of SED1-conjugated beads to intact zona pellucida, and (2) the binding of recombinant SED1 to distinct zona pellucida glycoproteins resolved by SDS-PAGE.

Figure 3:
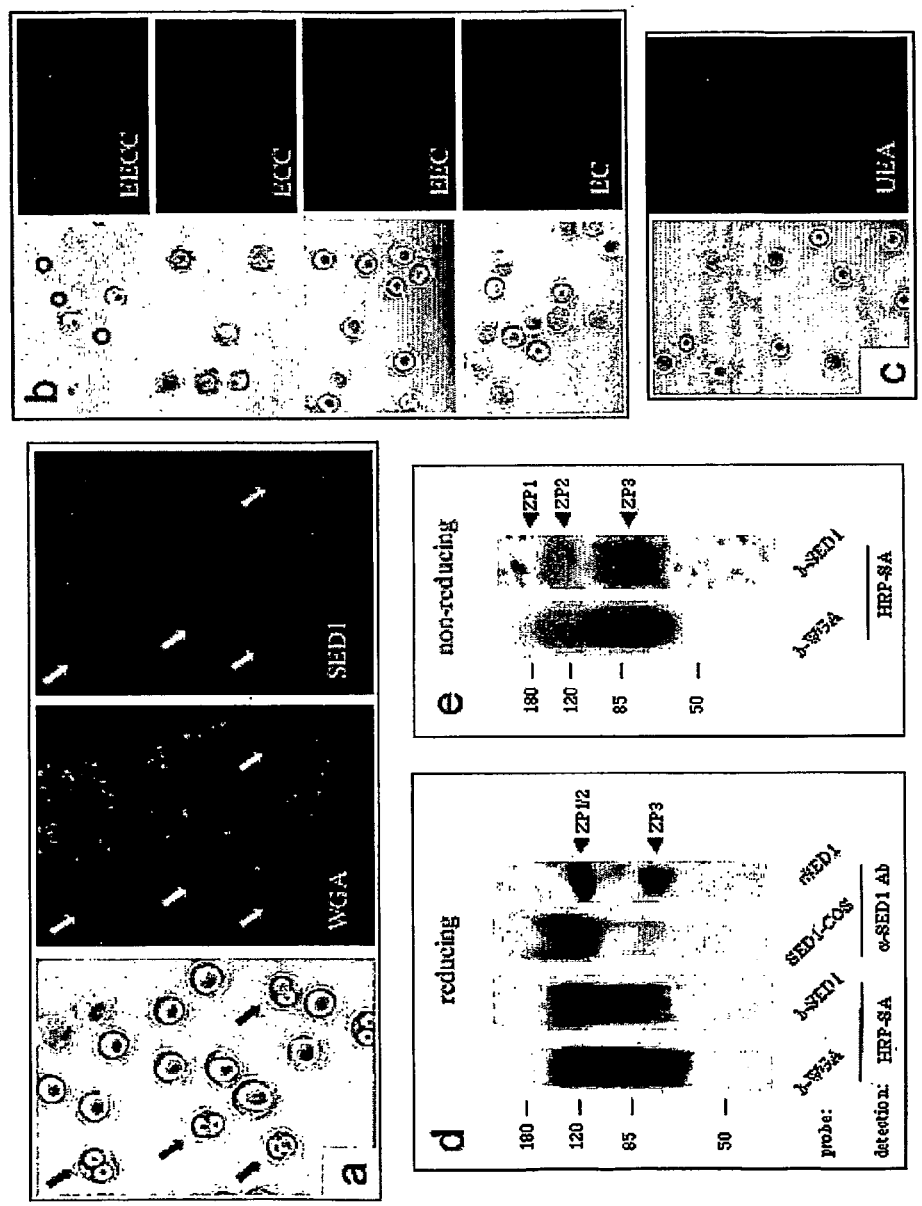
FIG. 3A is a panel of micrographs showing SED1-conjugated fluorescent beads (1 μm) readily adhere to the zona of unfertilized oocytes, but not to the zona of fertilized two-cell embryos (arrows).
FIG. 3B is a panel of micrographs showing beads conjugated with various truncated SED1 constructs also show specific binding to unfertilized oocytes, although constructs containing both C domains (C1C2) appear to bind more than do constructs with only the C1 domain.
FIG. 3C is a panel of micrographs showing UEA-I-conjugated beads do not bind, consistent with the lack of this epitope on the zona pellucida.
FIG. 3D is an immunoblot showing SED1 binds to the area corresponding to ZP1/ZP2 and to ZP3. Similarly, when ZP blots were probed with SED1 expressed either in COS-7 cells (SED1-COS) or in bacteria (rSED1) and detected with α-SED1 antibody, binding to ZP1/ZP2 and ZP3 under reducing conditions is seen.
FIG. 3E is an immunoblot showing recombinant (His)$_6$-SED1 (b-SED1) specifically bound ZP2 and ZP3, but not ZP1 under non-reducing conditions.

SED1-conjugated 1 μm fluorescent beads were added to droplets containing three sources of zona pellucida: zona pellucida fragments isolated from ovaries; intact, unfertilized ovulated oocytes; and two-cell embryos. Any nonadherent beads were removed by washing. SED1-conjugated fluorescent beads bound directly to the zona pellucida of unfertilized oocytes, as well as to zona fragments isolated from ovaries (not shown), but not to the zona pellucida of fertilized two-cell embryos (FIG. 3A). Beads conjugated with truncated forms of SED1 also bound to the oocyte zona pellucida, with constructs containing two discoidin/C domains showing higher binding than did constructs with only one discoidin/C domain (compare EECC and ECC versus EEC and EC, FIG. 3B). However, the nature of the assay prevented strict quantification of the binding affinities for the different truncated constructs. In any event, these results further implicate the discoidin/C domains in mediating attachment to the gamete surfaces. Consistent with this, the addition of RGD or RAD peptides had no effect on SED1 binding to unfertilized oocytes (not shown). As expected, WGA beads bound to unfertilized zona pellucida similar to SED1 beads, whereas control beads bound at background levels. Controls included unconjugated beads, as well as beads conjugated with Ulex europaeus agglutinin-1 (UEA1) lectin, BSA, or cytochrome C (data shown for UEA1-lectin, FIG. 4C).

To determine which of the three zona glycoproteins could serve as the putative ligand for SED1, ovarian, and incubated with recombinant SED1. When zona glycoproteins were resolved under reducing conditions, SED1 bound to glycoproteins comigrating as ZP1/ZP2 as well as ZP3 (FIG. 3D). Similar results were achieved using either biotinylated (His)$_6$-SED1 (D-SED1) detected by Streptavidin-HRP/ECL or recombinant (His)$_6$-SED1 (rSED1) detected by rabbit-anti-SED1 IgG and HRP-conjugated secondary antibodies (FIG. 3D). To avoid misleading interpretations due to the use of a bacterially expressed SED1, SED1 was expressed in COS-7 cells, which release budded membrane vesicles that are highly enriched for SED1 (Oshima et al., 2002). Similar to that seen with bacterially expressed SED1, COS-expressed SED1 (SED1-COS) bound ZP1/ZP2 and ZP3 under reducing conditions (FIG. 3D).

To distinguish between the ZP1 and ZP2 glycoproteins that migrate similarly under reducing conditions, zona glycoproteins were resolved under nonreducing conditions and probed with biotinylated (His)$_6$-SED1. Under nonreducing conditions, SED1 bound to ZP2 and ZP3. There was no reaction with ZP1 (FIG. 3E). SED1 binding to zona glycoproteins could also be demonstrated by performing the reciprocal incubation, i.e., adding solubilized murine zona pellucida to SED1 previously blotted onto PVDF membranes (not shown).

Example 8

Eliminating SED1 by Homologous Recombination Reduces Male Fertility In Vivo and Sperm-Egg Binding In Vitro The data thus far suggest that SED1 is localized to the sperm surface where it participates in binding to the zona pellucida of unfertilized oocytes. To test SED1 function more directly, the effects of targeted mutations in SED1 were analyzed on fertility and sperm-egg binding in vitro.

Figure 4:
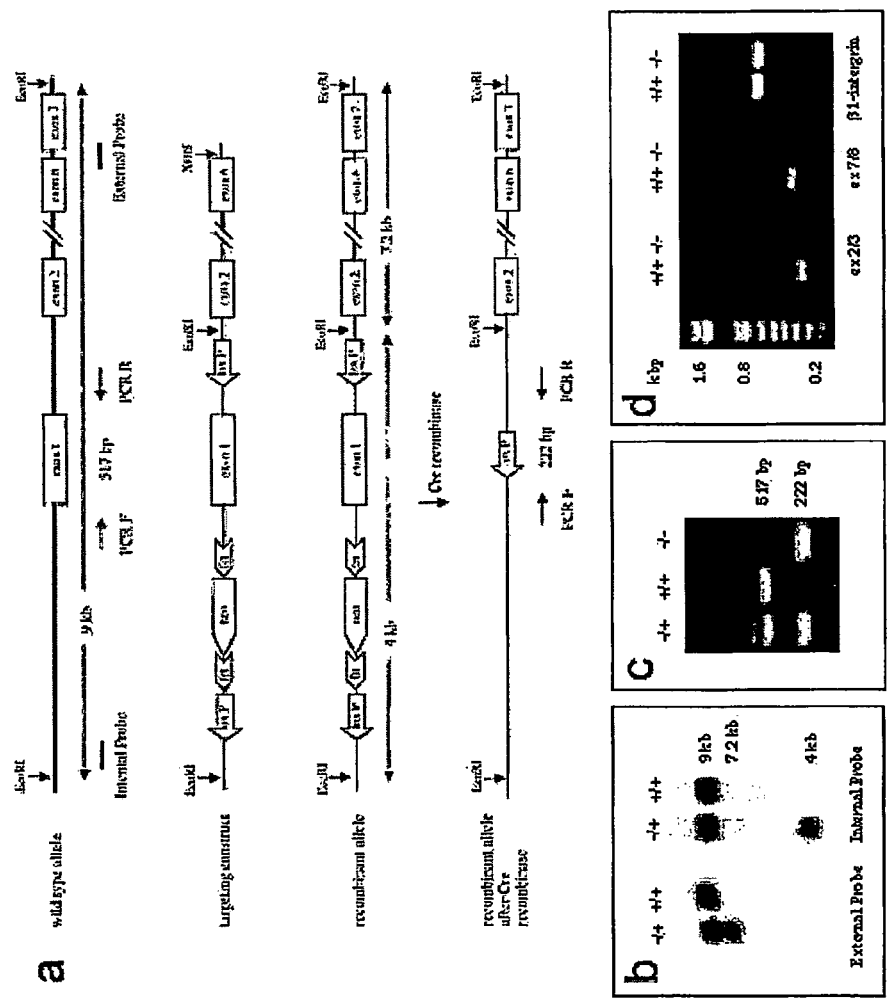
FIG. 4A is a diagram of an exemplary method for producing SED1 null mice.
FIG. 4B shows Southern blots following EcoRI digestion using external and internal probes.
FIG. 4C is an agarose gel showing PCR analysis detects a 517 bp product amplified from the wild-type allele and a 222 bp product amplified from the targeted allele.
FIG. 4D is an agarose gel showing RT-PCR analysis of testicular RNA illustrates the absence of SED1 transcripts, using primers spanning the EGF repeats (exons 2 and 3) as well as the discoidin/C domains (exons 7 and 8).

Two independent lines of SED1 null mice were created as described in the Experimental Procedures (FIG. 4). The deletion of the SED1 transcript in homozygous null mice was confirmed by RT-PCR of testicular cDNA using primers specific for the EGF domains (exons 2/3) and the discoidin/C domains (exons 7/8); primers specific for β-integrin served as control (FIG. 4D). Loss of the SED1 protein was confirmed by both immunoblotting and by indirect immunofluorescence of live sperm (FIGS. 6A and 6B).

Figure 5:
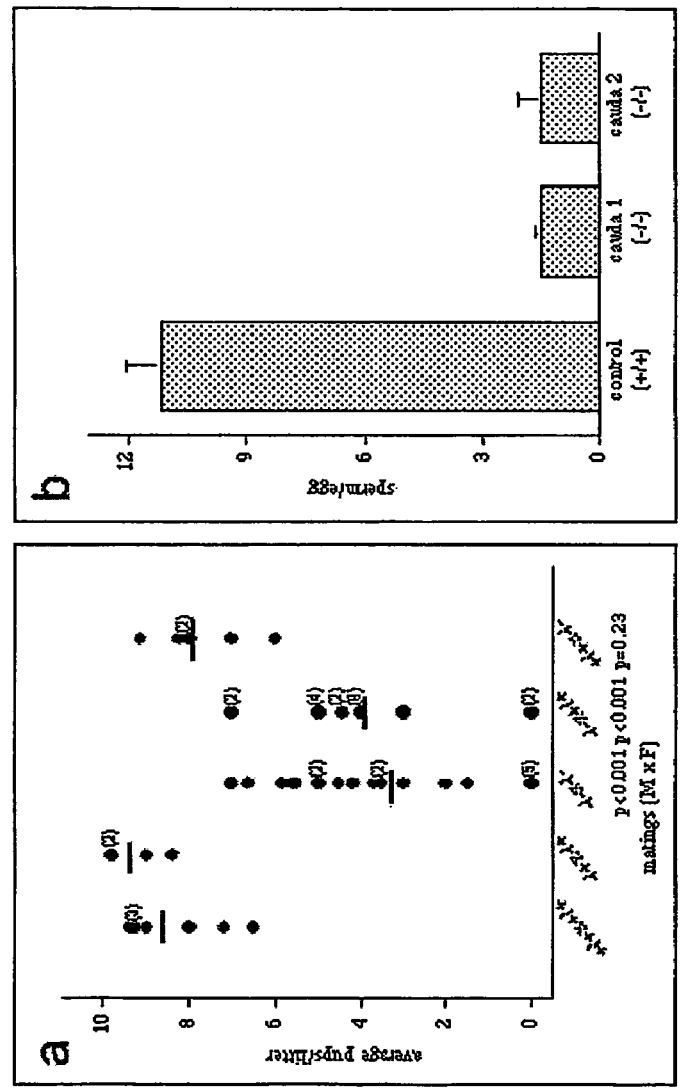
FIG. 5A shows the frequency distribution of litter sizes resulting from each breeding pair is presented. Each dot represents the average litter size resulting from a single breeding pair (0-20 litters/pair).
FIG. 5B is a bar graph showing sperm isolated from the cauda epididymis of SED1 males (−/−) bind to the zona pellucida at very low levels (1.45±0.56 sperm/egg), as compared to wild-type littermates (+/+) (11.2±0.85 sperm/egg). Error bars=±SEM.

Matings between sexually mature SED1 null littermates produced litter sizes (3.3±0.53 pups/litter, 62 litters) significantly smaller (p<0.001) than from control matings (+/+matings: 8.5±0.40 pups/litter, 24 litters; +/−matings: 9.3±0.35 pups/litter, 40 litters; +/+×+/−matings: 9.6±0.40 pups/litter, 10 litters, not shown). The reduced litter size from SED1 null matings could be attributed directly to the reduced fertility of the SED1 null males rather than reduced female fertility; i.e., matings between SED1 null males and wild-type females produced small litters (4.0±0.41 pups/litter, 31 litters, p<0.001), whereas SED1 null females mated to wild-type males generated near normal litter sizes (7.7±0.44 pups/litter, 26 litters, p=0.23). Both independent lines of SED1 null mice produced nearly identical average litter sizes, which could be attributed to the male parent (data not shown) (FIG. 5A).

Litter sizes resulting from the 16 control breeding pairs (all combinations of +/+ and +/− adults) were generally similar in size. In marked contrast, the litter sizes from the SED1 null matings varied considerably among the breeding pairs, ranging from no pups produced in 5 of 20 breeding pairs to litter sizes approaching the lower limit of normal variation. The variable phenotype in SED1 null males is not unprecedented (Nayernia et al., 2002; Pearse et al., 1997) and may reflect the segregation of genetic modifiers on the mosaic genetic background resulting from the incorporation of 129 ES cells into C57Bl/6 blastocysts (Wolfer et al., 2002). Testing this possibility must await the backcrossing of SED1 null animals onto a congenic background to determine if this results in a more penetrant male phenotype (i.e., higher rates of male sterility). Nevertheless, it is clear that the fertility of SED1 null males is greatly compromised, with some showing complete sterility whereas others show litter sizes still smaller than normal.

Example 9

Sperm from SED1 Null Males Binds Poorly to the Zona Pellucida

Figure 6:
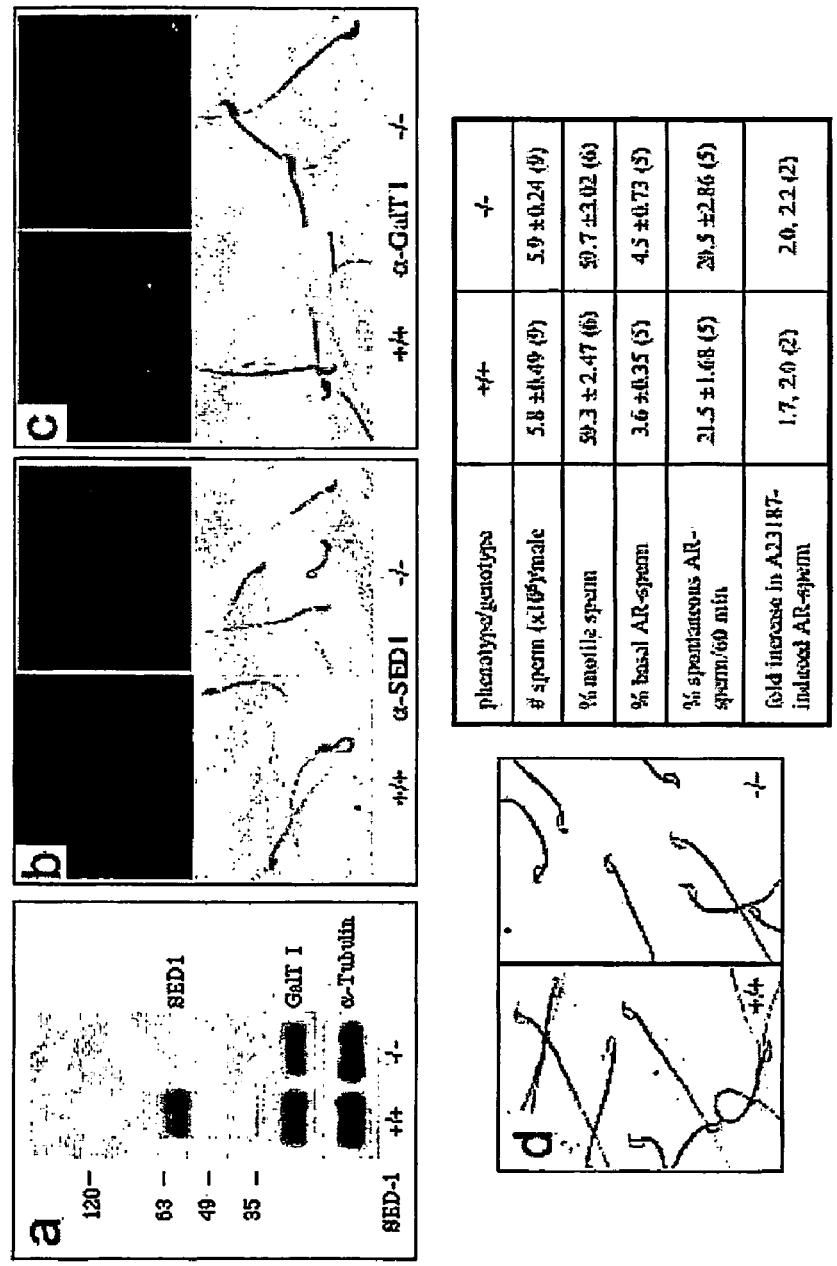
FIG. 6A is an immunoblot showing the presence or absence of SED1 and GalT in sperm from wild type and SED1 null mice.
FIGS. 6B and 6C are indirect immunofluorescence micrographs showing unfixed SED1 null sperm are devoid of SED1 but express GalT I normally.
FIG. 6D are micrographs showing wild-type and SED1 null males produced similar numbers of cauda epididymal sperm, which showed similar levels of motility, as well as the extent of basal, spontaneous, and ionophore-induced acrosome reactions (table, number of males assayed given in parentheses).

The reduced fertility of SED1 males is consistent with the function of SED1 in sperm-egg binding. The ability of sperm from wild-type and SED1 null males to bind the zona pellucida in vitro was compared. Sperm isolated from each SED1 null cauda epididymis was assayed separately, rather than pooled as is normally done with wild-type sperm, in case there were differences between the two cauda. SED1 null sperm bound to the zona pellucida at levels close to background, i.e., 1.45±0.56 sperm/egg versus 11.2±0.85 sperm/egg using wild-type sperm (FIG. 5B). Sperm isolated from both SED1 null cauda epididymides displayed similar levels of decreased sperm/egg binding. The reduced binding of SED1 null sperm to the egg coat was not the secondary result of defective sperm morphology; number; percent motility; or the level of basal, spontaneous or ionophore-induced acrosome reactions, all of which were indistinguishable between normal and SED1 null sperm (FIG. 6). Collectively, these results show that sperm from SED1 null mice are relatively unable to bind to the zona pellucida, both confirming its role in normal sperm-egg adhesion and offering a mechanism to account for the reduced male fertility in vivo.

GalT I on the sperm surface functions as a receptor for the zona pellucida glycoprotein ZP3 (Miller et al., 1992), an observation that is supported by both gain-of-function and loss-of-function GalT I mutations (Lu and Shur, 1997; Shi et al., 2001; Youakim et al., 1994). However, sperm from GalT I null males still bind to the zona pellucida, although they fail to bind ZP3 or undergo zona-induced acrosomal exocytosis (Lu and Shur, 1997). This led us to search for novel sperm receptors for the egg coat, such as SED1. Since it has been reported that elimination of some sperm proteins (i.e., the ADAMS) can have unanticipated effects on the expression of unrelated sperm components (Nishimura et al., 2001), the elimination of SED1 was investigated to determine any unanticipated effects on GalT 1 expression or function. This was shown not to be the case, since SED1 null sperm express GalT I normally by both immunoblot analysis and indirect immunofluorescence of live sperm (FIGS. 6A and 6C). In addition, the binding of GalT1 null sperm to the zona is inhibited by anti-SED1 IgG (33% of control binding at 200 μg/ml versus 91% for preimmune IgG), recombinant SED1 (27% of control at 6 μg/ml), and the EEC truncated protein (21% of control at 3.8 μg/ml). Thus, the expression and function of GalT I and SED1 are independent of one another, consistent with their having distinct roles during sperm-egg binding.

SED1 As a Gamete Adhesin

The results presented here support the involvement of SED1 in mammalian gamete recognition and/or adhesion. SED1 is homologous to a small group of bimotif secreted proteins containing N-terminal EGF domains and C-terminal discoidin/complement domains (Andersen et al., 1997, 2000; Couto et al., 1996; Ogura et al., 1996; Stubbs et al., 1990). SED1 is expressed in the Golgi complex of spermatogenic cells and is likely secreted onto the maturing sperm surface. The most abundant expression of SED1 in the male reproductive tract occurs in the initial segment of the epididymis, where sperm are exposed to high levels of secreted SED1. The presence of SED1 immunoreactivity in the adsorptive clear cells of the cauda epididymis suggests that excess SED1 is removed from the sperm environment before they leave the epididymis. On mature sperm, SED1 expression is confined to the sperm plasma membrane overlying the acrosome, the known location for sperm binding to the egg coat. Recombinant SED1, expressed in either bacteria or insect cells, competitively inhibits sperm-egg binding, as do anti-SED1 antibodies. The biological activity of SED1 requires the discoidin/C domains, which appear to be responsible for SED1 attachment to the sperm membrane and to the zona pellucida matrix. Direct binding of SED1 to the zona pellucida of unfertilized, but not fertilized, eggs is consistent with its role in sperm binding, and immunoblot overlay assays suggest that SED1 recognizes the ZP2 and ZP3 glycoprotein families. Given the ability of discoidin/C domains to bind complex carbohydrates matrices (Fuentes-Prior et al., 2002; Reitherman et al., 1975), it is most likely that SED1 is binding to the carbohydrates residues of ZP2 and ZP3.

Independent of its zona binding specificity, the function of SED1 during fertilization was directly tested by creating SED1 null mice and analyzing their fertility. All SED1 null males produced smaller litters than controls, although the average litter size per male varied considerably, ranging from no pups born (apparent sterility) to litter sizes approaching the lower limit of normal. This variability is most likely due to genetic factors segregating on the mosaic 129/B6 background as was shown to be the case for at least two other targeted mutations in sperm. Mice bearing mutations in either the Sprm-1 transcription factor (Pearse et al., 1997) or the Smcp mitochondrial protein (Nayemia et al., 2002) lead to male sterility only when inbred on the 129/Sv line. Despite the variability in male fertility in vivo, sperm from all SED1 null males tested showed near background levels of binding to the zona pellucida in vitro, consistent with a role for SED1 in sperm-egg binding.

SED1 and GalT I Function Independently

SED1 expression and function is independent of GalT I, a previously identified sperm receptor for the zona pellucida glycoprotein, ZP3 (Miller et al., 1992). GalT I is expressed normally on SED1 null sperm, and GalT I null sperm are equally sensitive to inhibition by SED1 antagonists, as are wild-type sperm. Analysis of GalT I function suggests that it acts specifically as a signaling component for ZP3-dependent acrosomal exocytosis (Gong et al., 1995; Lu and Shur, 1997; Shi et al., 2001; Youakim et al., 1994), since GalT I null sperm are unable to bind ZP3 in solution or undergo zona-induced acrosomal exocytosis, although they still bind to the egg coat. In contrast to GalT I, SED1 appears to function during the initial adhesion between the sperm and egg coat. Consequently, these results suggest the simple working model that sperm binding to the egg coat requires at least two distinct binding events: initial adhesion between the gametes facilitated by SED1 and a subsequent interaction between GalT I (and possibly other sperm components) and ZP3 oligosaccharides, leading to GalT I aggregation and acrosomal exocytosis. If sperm-egg binding involves at least two distinct molecular interactions, it is unclear why reagents against either one (i.e., GalT I or SED1) are able to inhibit sperm-egg binding when assayed individually. Possibly, these two molecular complexes functionally interact or some of these inhibitory reagents may sterically interfere with adjacent sperm surface components. Alternatively, the overall process of sperm-egg binding may result from the summation of temporally-specific stages, each defined by a unique molecular interaction, that are currently below the resolution of in vitro sperm-egg binding assays. In an analogous manner, a multiplicity of molecular interactions facilitating gamete adhesion is reminiscent of the sequential requirement bf selectins and integrins during lymphocyte interactions with the vascular endothelium (Worthylake and Burridge, 2001).

SED1 Functional Domains

The involvement of SED1 in the initial adhesion of sperm to the extracellular coat of the egg is consistent with studies of two SED1 homologs, lactadherin (also known as PAS 6/7) and Dell, which are thought to act as bimotif adhesive proteins that facilitate cell adhesion to the extracellular matrix (Andersen et al., 1997; 2000; Penta et al., 1999). In particular, the discoidin/C domains are found in a wide variety of proteins and are thought to mediate protein binding to cell membranes and to extracellular matrix components (Fuentes-Prior et al., 2002). Recent structural analysis of these domains indicates that they fold into an eight-stranded antiparallel β barrel from which two (or three) hairpin spikes project that present polypeptide-specific residues for interacting with various binding surfaces. For example, the spikes found in the C2 domain of complement possess hydrophobic residues that intercalate into the lipid bilayer, surrounded by a ring of charged residues that dock with phosphatidylserine headgroups (Macedo-Ribeiro et al., 1999; Pratt et al., 1999). The F5/8 C domains in "discoidin," the galactose binding lectin from Dictyostelium, display a completely different binding specificity in that spikes projecting from the discoidin p barrel coordinate binding to galactose residues rather than to membrane phospholipids (Fuentes-Prior et al., 2002; Reitherman et al., 1975). Similar to that seen in the discoidin lectin, the chitobiase enzyme from Arthrobacter utilizes a discoidin/C domain to attach to glycans terminating in sialic acid, galactose, and N-acetylglucosamine (Lonhienne et al., 2001). In all instances, hypervariable spikes project from the eight-stranded β barrel core and are thought to determine the specificity of binding to membranes and to the extracellular matrix (Fuentes-Prior et al., 2002).

It is, therefore, not surprising that the discoidin/C domains appear to be required for SED1 biological activity, based upon the ability of discoidin/C-containing constructs to competitively inhibit sperm-egg binding as well as to bind directly to the zona pellucida. There is no evidence in this system that SED1 function involves RGD recognition by integrins. Although there have been some preliminary reports of integrins on human sperm membranes (Fusi et al., 1996; Trubner et al., 1997), their presence has not been documented in mouse. Furthermore, the a subunit (i.e., $\alpha_v$) reported to bind the RGD domain in lactadherin (Andersen et al., 1997) and Dell (Penta et al., 1999) is not present on the surface of fresh, ejaculated, or capacitated human sperm (Fusi et al., 1996). More directly, the addition of RGD had no specific effect on SED1 association with sperm. Consequently, the data are consistent with a working model in which the discoidin/C domains mediate interactions with both the sperm membrane and the egg coat. In this regard, both of the SED1 discoidin/C domains have the amino acids required to form the two hairpin loops that present site-specific residues for docking to membranes and/or matrices (Fuentes-Prior et al., 2002).

Models for SED1 Function during Gamete Adhesion

Figure 7:
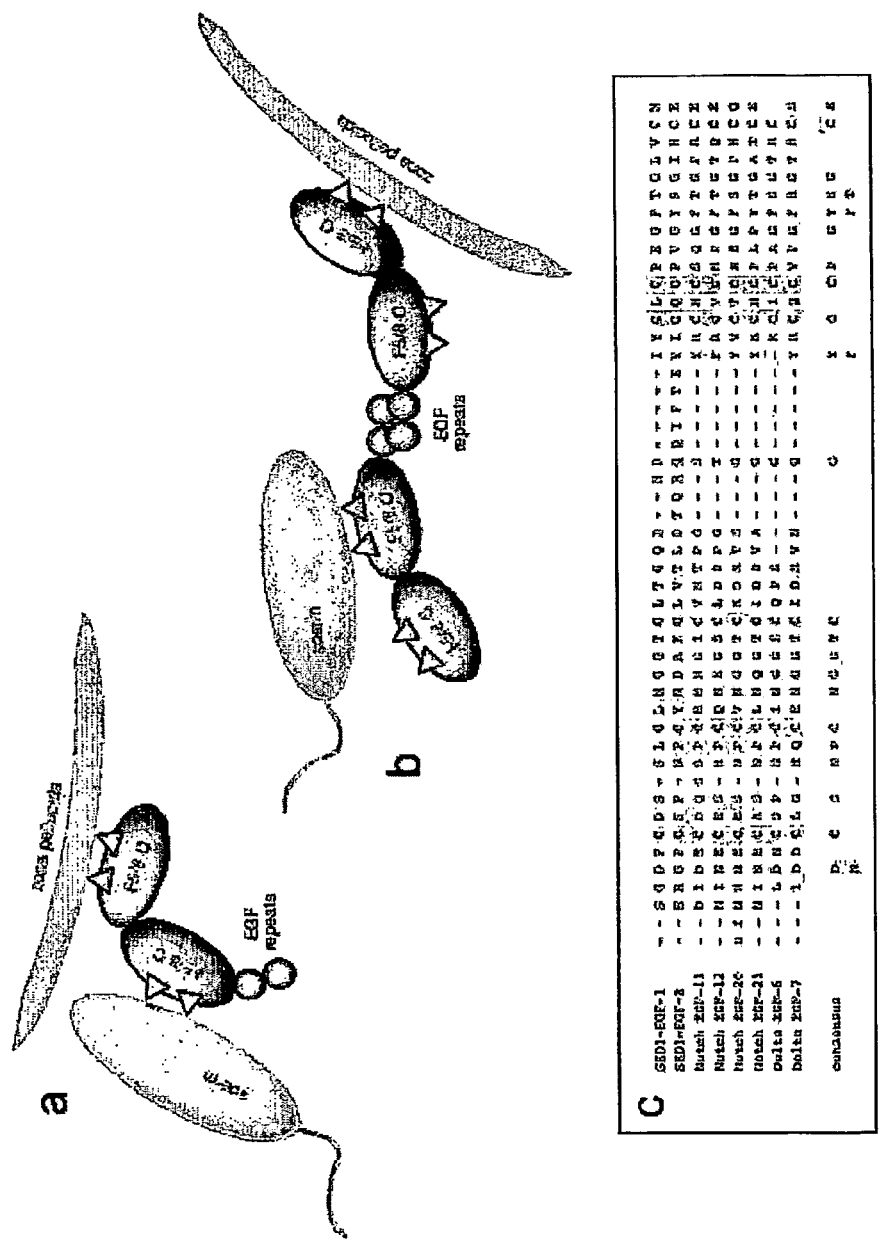
FIGS. 7A and 7B show diagrams of exemplary models for SED1 function during sperm-egg binding.
FIG. 7C shows SED1 EGF repeats 1 and 2 are aligned with a variety of Notch-family EGF domains.
Figure 8:
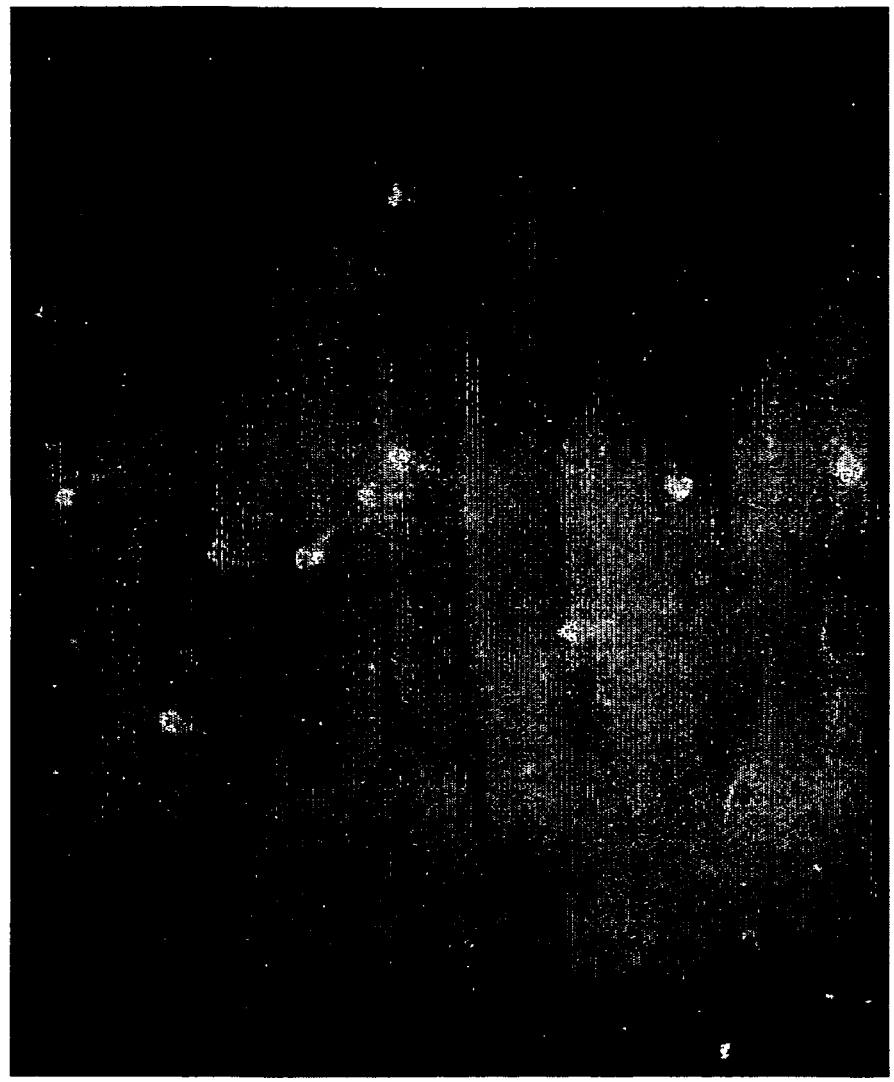
FIG. 8 is an immunofluorescence micrograph showing that antibodies to SED1 recognize an epitope on human sperm.

Some working models for SED1 function can be developed from the results presented here, from SED1 sequence analysis, and from studies of SED1 homologs in other systems. Given that the discoidin/C domains can account for SED1 binding to both the sperm membrane and the zona pellucida, the simplest model proposes that SED1 functions as a monomer, whereby the two discoidin/C domains of a single SED1 polypeptide are sufficient to bind sperm to the zona pellucida (FIG. 7A). Since constructs containing both C domains (C1 C2) show increased binding to the zona relative to constructs with only the C1 domain (FIG. 3), it is possible that the C2 domain has greater affinity for the zona, whereas the C1 domain mediates attachment to the sperm membrane.

Alternatively, SED1 may mediate sperm-egg binding as a dimer, or oligomer, as has been illustrated for the epithelial cell adhesion molecule, Ep-CAM (FIG. 7B). Ep-CAM mediates adhesions by homophilic binding between the two Notch-like EGF repeats; the first EGF domain appears responsible for interactions with Ep-CAM on apposing cells, whereas the second EGF domain is thought to mediate lateral oligomerization of Ep-CAMs. within the membrane (Balzar et al., 2001). This is particularly relevant to understanding SED1 function, since both EGF repeats in SED1 contain classic Notch-like consensus sequences (Balzar et al., 2001), and only two EGF repeats are required for Notch-like protein-protein binding (Balzar et al., 2001; Lawrence etal., 2000) (FIG. 7C). The first EGF repeat of SED1 contains the Notch O-glycosylation consensus sequence, suggesting that O-glycosylation may regulate SED1 dimer (or oligomer) formation, analogous to its regulation of Notch-ligand binding (Haltiwanger, 2002).

In either scenario, one discoidin/C domain (e.g., C1) is postulated to mediate SED1 attachment to sperm, whereas a second discoidin/C domain (e.g., C2), either within the SED1 monomer or dimer partner, is exposed for association with the zona pellucida (FIG. 7B). Recent crystallographic data suggests that the exposed, or unoccupied, discoidin/C domain remains in a cryptic, or closed, conformation until presentation to its binding surface (i.e., zona pellucida), which stabilizes the active, or open, binding conformation (Fuentes-Prior et al., 2002).

Neither EGF repeats or discoidin/C domains have been implicated in mammalian fertilization previously, although a sperm surface protein containing EGF repeats is thought to be required for sperm-egg binding in C. elegans (Singson et al., 1998). Therefore, the identification of SED1 proposes a previously unappreciated mechanism for mammalian gamete recognition, which takes advantage of highly conserved protein motifs that facilitate binding to a wide range of cell surfaces and extracellular matrices.

REFERENCES

The references identified throughout this disclosure are incorporated by reference in their entirety where permissible.

Andersen, M. H., Berglund, L, Rasmussen, J. T., and Petersen, T. E. (1997). Bovine PAS-6/7 binds $\alpha_v\beta_5$ integrin and anionic phospholip-ids through two domains. Biochemistry 36, 5441-5446.

Andersen, M. H., Graversen, H., Fedosov, S. N., Petersen, T. E., and Rasmussen, J. T. (2000). Functional analyses of two cellular binding domains of bovine Lactadherin. Biochemistry 39, 6200-6206.

Aviles, M., Jaber, L, Castells, M. T., Ballesta, J., and Kan, F. W. (1997). Modifications of carbohydrate residues and ZP2 and ZP3 glycoproteins in the mouse zona pellucida after fertilization. Biol. Reprod. 57, 1155-1163.

Balzar, M., Briaire-de Bruijn, l.H., Rees-Bakker, H. A., Prins, F. A., Helfrich, W., de Leij, L, Riethmuller, G., Alberti, S., Wamaar, S. O., Fleuren, G. J., and Litvinov, S. V. (2001). Epidermal growth factor-like repeats mediate lateral and reciprocal interactions of Ep-CAM molecules in homophilic adhesions. Mol. Cell. Biol. 21, 2570-2580.

Buckley, C. D., Pilling, D., Henriquez, N. V., Parsonage, G., Threlfall, K., Scheel-Toellner, D., Simmons, D. L., Akbar, A. M., Lord, J. M., and Salmon, M. (1999). RGD peptides induce apoptosis by direct cas-pase-3 activation. Nature 397, 534-539.

Couto, J. R., Taylor, M. R., Godwin, S. G., Ceriani, R.L, and Peterson, J. A. (1996). Cloning and sequence analysis of human breast epithelial antigen BA46 reveals an RGD cell adhesion sequence presented on an epidermal growth factor-like domain. DMA Cell Biol. 15, 281-286.

Ensslin, M., Vogel, T., Calvete, J. J., Thole, H. H., Schmidtke, J., Matsuda, T., and Topfer-Petersen, E. (1998). Molecular cloning and characterization of P47, a novel boar sperm-associated zona pellucida-binding protein homologous to a family of mammalian secretory proteins. Biol. Reprod. 58, 1057-1064.

Florman, H. M., and Wassarman, P. M. (1985). 0-linked oligosaccha-rides of mouse egg ZP3 account for its sperm receptor activity. Cell 41, 313-324. Fuentes-Prior, P., Fujikawa, K., and Pratt, K. P. (2002). New insights into binding interfaces of coagulation factors V and VIII and their homologues-lessons from high resolution crystal structures. Curr. Protein Pept. Sci. 3, 313-339.

Fusi, F. M., Tamburini, C., Mangili, F., Montesano, M., Ferrari, A., and Bronson, R. A. (1996). The expression of alpha v, alpha 5, beta 1, and beta 3 integrin chains on ejaculated human spermatozoa varies with their functional state. Mol. Hum. Reprod. 2,169-175.

Gong, X., Dubois, D. H., Miller, D. J., and Shur, B. D. (1995). Activation of a G protein complex by aggregation of $\beta$1,4-galactosyltransferase on the surface of sperm. Science 269,1718-1721.

Haltiwanger, R. S. (2002). Regulation of signal transduction pathways in development by glycosylation. Curr. Opin. Struct. Biol. 12, 593-598. Janssen, P. J., Brinkmann, A. O., Boersma, W. J., and Van der Kwast, T. H. (1994). Immuno-histochemical detection of the androgen receptor with monoclonal antibody F39.4 in routinely processed, paraffin-embedded human tissues after microwave pre-treatment. J. Histochem. Cytochem. 42, 1169-1175.

Johnston, D. S., Wright, W. W., Shaper, J. H., Hokke, C. H., Van den Eijnden, D. H., and Joziasse, D. H. (1998). Murine spermzona binding, a fucosyl residue is required for a high affinity sperm-binding ligand. A second site on sperm binds a nonfucosylated, (3-galactosyl-capped oligosaccharide. J. Biol. Chem. 273,1888-1895.

Larson, J. L., and Miller, D. J. (1999). Simple histochemical stain for acrosomes on sperm from several species. Mol. Reprod. Dev. 52, 445-449.

Lawrence, N., Klein, T., Brennan, K., and Martinez Arias, A. (2000). Structural requirements for notch signalling with Delta and Serrate during the development and patterning of the wing disc of Drosophila. Development 727, 3185-3195.

Lonhienne, T., Zoidakis, J., Vorgias, C. E., Feller, G., Gerday, C., and Bouriotis, V. (2001). Modular structure, local flexibility and cold-activity of a novel chitobiase from a psychrophilic Antarctic bacterium. J. Mol. Biol. 370, 291-297.

Lu, Q., and Shur, B. D. (1997). Sperm from $\beta$1,4-galactosyltransferase-null mice are refractory to ZP3-induced acrosome reactions and penetrate the zona pellucida poorly. Development 724,41214131. Macedo-Ribeiro, S., Bode, W., Huber, R., Quinn-Allen, M. A., Kim, S. W., Ortel, T. L., Bourenkov, G. P., Bartunik, H. D., Stubbs, M. T., Kane, W. H., and Fuentes-Prior, P. (1999). Crystal structures of the membrane-binding C2 domain of human coagulation factor V. Nature 402, 434-439.

Miller, D. J., Macek, M. B., and Shur, B. D. (1992). Complementarity between sperm surface $\beta$1,4-galactosyltransferase and egg-coat ZP3 mediates sperm-egg binding. Nature 357, 589-593.

Nagdas, S. K., Araki, Y., Chayko, C. A., Orgebin-Crist, M. C., and Tulsiani, D. R. P. (1994). 0-linked trisaccharide and N-linked poly-N-acetyllactosaminyl glycans are present on mouse ZP2 and ZP3. Biol. Reprod. 57, 262-272.

Nayemia, K., Adham, l.M., Burkhardt-Gottges, E., Neesen, J., Rieche, M., Wolf, S., Sancken, U., Kleene, K., and Engel, W. (2002). Asthenozoospermia in mice with targeted deletion of the sperm mitochondrion-associated cysteine-rich protein (Smcp) gene. Mol. Cell. Biol. 22, 3046-3052.

Nelles, L. P., and Bamburg, J. R. (1976). Rapid visualization of protein-dodecyl sulfate complexes in polyacrylamide gels. Anal. Biochem. 73, 522-531.

Nishimura, H., Cho, C., Branciforte, D. R., Myles, D. G., and Primakoff, P. (2001). Analysis of loss of adhesive function in sperm lacking cyritestin orfertilin beta. Dev. Biol. 233, 204-213.

Ogura, K., Nara, K., Watanabe, Y., Kohno, K., Tai, T., and Sanai, Y. (1996). Cloning and expression of cDNA for 0-acetylation of GD3 ganglioside. Biochem. Biophys. Res. Commun. 225, 932-938.

Oshima, K., Aoki, N., Kato, T., Kitajima, K., and Matsuda, T. (2002). Secretion of a peripheral membrane protein, MFG-E8, as a complex with membrane vesicles. Eur. J. Biochem. 269, 1209-1218.

Pearse, R. V., 2nd, Drolet, D. W., Kalla, K. A., Hooshmand, F., Bermingham, J. R., Jr., and Rosenfeld, M. G. (1997). Reduced fertility in mice deficient for the POU protein sperm-1. Proc. Natl. Acad. Sci. USA 94, 7555-7560.

Penta, K., Varner, J. A., Liaw, L., Hidai, C., Schatzman, R., and Quertermous, T. (1999). Dell induces integrin signaling and angiogenesis by ligation of aV(33. J. Biol. Chem. 274, 11101-11109.

Pratt, K. P., Shen, B. W., Takeshima, K., Davie, E. W., Fujikawa, K., and Stoddard, B. L. (1999). Structure of the C2 domain of human factor VIII at 1.5 A resolution. Nature 402, 439-442.

Primakoff, P., and Myles, D. G. (2002). Penetration, adhesion, and fusion in mammalian sperm-egg interaction. Science 296, 2183-2185.

Rankin, T. L, long, Z. B., Castle, P. E., Lee, E., Gore-Langton, R., Nelson, L. M., and Dean, J. (1998). Human ZP3 restores fertility in Zp3 null mice without affecting order-specific sperm binding. Development 125, 2415-2424.

Rankin, T.L, Coleman, J. S., Epifano, O., Hoodbhoy, T., Turner, S. G., Castle, P. E., Lee, E., Gore-Langton, R., and Dean, J. (2003). Fertility and taxon-specific sperm binding persist after replacement of mouse sperm receptors with human homologs. Dev. Cell 5, 33-43.

Reitherman, R. W., Rosen, S. D., Frasier, W. A., and Barondes, S. H. (1975). Cell surface species-specific high affinity receptors for discoidin: developmental regulation in Dictyostelium discoideum. Proc. Natl. Acad. Sci. USA 72, 3541-3545.

Robaire, B., and Hermo, L. (1994). Efferent ducts, epididymis, and vas deferens: structure, functions and their regulations. In The Physiology of Reproduction. E. Knobil and J. Neill, eds. (New York: Raven Press), pp. 999-1080.

Shi, X., Amindari, S., Paruchuru, K., Skalla, D., Shur, B. D., and Miller, DJ. (2001). Cell surface (β1,4-galactosyl-transferase-1 activates G-protein-dependent exocytotic signaling. Development 128, 645-654.

Singson, A., Mercer, K. B., and L'Hemault, S. W. (1998). The C. elegans spe-9 gene encodes a sperm transmembrane protein that contains EGF-like repeats and is required for fertilization. Cell 93, 71-79.

Stubbs, J. D., Lekutis, C., Singer, K. L., Bui, A., Yuzuki, D., Srinivasan, U., and Parry, G. (1990). cDNA cloning of a mouse mammary epithelial cell surface protein reveals the existence of epidermal growth factor-like domains linked to factor VIII-like sequences. Proc. Natl. Acad. Sci. USA 87, 8417-8421.

Trubner, M., Glander, H. J., and Schaller, J. (1997). Localization of adhesion molecules on human spermatozoa by fluorescence microscopy. Andrologia 29, 253-260.

Wassarman, P. M., Jovine, L., and Litscher, E. S. (2001). A profile of fertilization in mammals. Nat. Cell Biol. 3, E59-E64.

Wolfer, D. P., Crusio, W. E., and Lipp, H. P. (2002). Knockout mice: simple solutions to the problems of genetic background and flanking genes. Trends Neurosci. 25, 336-340.

Worthylake, R. A., and Burridge, K. (2001). Leukocyte transendothelial migration: orchestrating the underlying molecular machinery. Curr. Opin. Cell Biol. 13, 569-577.

Youakim, A., Hathaway, H. J., Miller, D. J., Gong, X., and Shur, B. D. (1994). Overexpressing sperm surface (β1,4 galactosyltransferase in transgenic mice affects multiple aspects of sperm-egg interactions. J. Cell Biol. 126, 1573-1584.

We claim:

1. A pharmaceutical composition comprising: an isolated SED1 polypeptide having an amino acid sequence selected from SEQ ID NOs: 2, 4, 5, 6, or 7, wherein the polypeptide is in an amount effective to inhibit mammalian gamete adhesion.

2. The composition of claim 1, further comprising a pharmaceutically acceptable carrier or excipient.

3. The composition of claim 1, wherein the polypeptide competitively inhibits in vivo or in vitro binding of sperm to unfertilized zona pellucida.

4. The composition of claim 1, wherein the isolated SED1 polypeptide compound binds to male gametes, female gametes, male and female gametes, zona pellucida, or combinations thereof.

5. The composition of claim 1, wherein the isolated SED1 polypeptide is a recombinant polypeptide.

* * * * *

SEQUENCE LISTING

```
<160> NUMBER OF SEQ ID NOS: 9

<210> SEQ ID NO 1
<211> LENGTH: 1281
<212> TYPE: DNA
<213> ORGANISM: Mus musculus

<400> SEQUENCE: 1
atgcaggtct cccgtgtgct ggccgcgctg tgcggcatgc tactctgcgc ctctggcctc      60
ttcgccgcgt ctggtgactt ctgtgactcc agcctgtgcc tgaacggtgg cacctgcttg     120
acgggccaag acaatgacat ctactgcctc tgccctgaag gcttcacagg ccttgtgtgc     180
aatgagactg agagggacc atgctcccca aaccctttgct acaatgatgc caaatgtctg     240
gtgactttgg acacacagcg tggggacatc ttcaccgaat acatctgcca gtgccctgtg     300
ggctactcgg gcatccactg tgaaaccggt tgttctacac agctgggcat ggaaggggggc     360 gccattgctg attcacagat ttccgcctcg tctgtgtata tgggtttcat gggcttgcag     420
cgctggggcc cggagctggc tcgtctgtac cgcacaggga tcgtcaatgc ctggacagcc     480
agcaactatg atagcaagcc ctggatccag gtgaaccttc tgcggaagat gcgggtatca     540
ggtgtgatga cgcaggtgc cagccgtgcc gggagggcgg agtacctgaa gaccttcaag     600
gtggcttaca gcctcgacgg acgcaagttt gagttcatcc aggatgaaag cggtggagac     660
aaggagtttt tgggtaacct ggacaacaac agcctgaagg ttaacatgtt caacccgact     720
ctggaggcac agtacataag gctgtaccct gtttcgtgcc accgcggctg caccctccgc     780
ttcgagctcc tgggctgtga gttgcacgga tgttctgagc cctgggcct gaagaataac     840 acaattcctg acagccagat gtcagcctcc agcagctaca agacatggaa cctgcgtgct     900
tttggctggt acccccactt gggaaggctg gataatcagg gcaagatcaa tgcctggacg     960
gctcagagca acagtgccaa ggaatggctg caggttgacc tgggcactca gaggcaagtg    1020
```

-continued

```
acaggaatca tcacccaggg ggcccgtgac tttggccaca tccagtatgt ggcgtcctac    1080
aaggtagccc acagtgatga tggtgtgcag tggactgtat atgaggagca aggaagcagc    1140
aaggtcttcc agggcaactt ggacaacaac tcccacaaga agaacatctt cgagaaaccc    1200
ttcatggctc gctacgtgcg tgtccttcca gtgtcctggc ataaccgcat caccctgcgc    1260
ctggagctgc tgggctgtta a                                              1281
```

<210> SEQ ID NO 2
<211> LENGTH: 426
<212> TYPE: PRT
<213> ORGANISM: mus musculus

<400> SEQUENCE: 2

```
Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Thr Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Gly Cys Ser
            100                 105                 110

Thr Gln Leu Gly Met Glu Gly Ala Ile Ala Asp Ser Gln Ile Ser
        115                 120                 125

Ala Ser Ser Val Tyr Met Gly Phe Met Gly Leu Gln Arg Trp Gly Pro
    130                 135                 140

Glu Leu Ala Arg Leu Tyr Arg Thr Gly Ile Val Asn Ala Trp Thr Ala
145                 150                 155                 160

Ser Asn Tyr Asp Ser Lys Pro Trp Ile Gln Val Asn Leu Leu Arg Lys
                165                 170                 175

Met Arg Val Ser Gly Val Met Thr Gln Gly Ala Ser Arg Ala Gly Arg
            180                 185                 190

Ala Glu Tyr Leu Lys Thr Phe Lys Val Ala Tyr Ser Leu Asp Gly Arg
        195                 200                 205

Lys Phe Glu Phe Ile Gln Asp Glu Ser Gly Gly Asp Lys Glu Phe Leu
    210                 215                 220

Gly Asn Leu Asp Asn Asn Ser Leu Lys Val Asn Met Phe Asn Pro Thr
225                 230                 235                 240

Leu Glu Ala Gln Tyr Ile Arg Leu Tyr Pro Val Ser Cys His Arg Gly
                245                 250                 255

Cys Thr Leu Arg Phe Glu Leu Leu Gly Cys Glu Leu His Gly Cys Ser
            260                 265                 270

Glu Pro Leu Gly Leu Lys Asn Asn Thr Ile Pro Asp Ser Gln Met Ser
        275                 280                 285

Ala Ser Ser Tyr Lys Thr Trp Asn Leu Arg Ala Phe Gly Trp Tyr
    290                 295                 300

Pro His Leu Gly Arg Leu Asp Asn Gln Gly Lys Ile Asn Ala Trp Thr
305                 310                 315                 320
```

```
Ala Gln Ser Asn Ser Ala Lys Glu Trp Leu Gln Val Asp Leu Gly Thr
            325                 330                 335

Gln Arg Gln Val Thr Gly Ile Ile Thr Gln Gly Ala Arg Asp Phe Gly
        340                 345                 350

His Ile Gln Tyr Val Ala Ser Tyr Lys Val Ala His Ser Asp Asp Gly
            355                 360                 365

Val Gln Trp Thr Val Tyr Glu Glu Gln Gly Ser Ser Lys Val Phe Gln
370                 375                 380

Gly Asn Leu Asp Asn Asn Ser His Lys Lys Asn Ile Phe Glu Lys Pro
385                 390                 395                 400

Phe Met Ala Arg Tyr Val Arg Val Leu Pro Val Ser Trp His Asn Arg
                405                 410                 415

Ile Thr Leu Arg Leu Glu Leu Leu Gly Cys
            420                 425

<210> SEQ ID NO 3
<211> LENGTH: 404
<212> TYPE: PRT
<213> ORGANISM: mus musculus

<400> SEQUENCE: 3

Ala Ser Gly Asp Phe Cys Asp Ser Ser Leu Cys Leu Asn Gly Gly Thr
1               5                   10                  15

Cys Leu Thr Gly Gln Asp Asn Asp Ile Tyr Cys Leu Cys Pro Glu Gly
            20                  25                  30

Phe Thr Gly Leu Val Cys Asn Glu Thr Glu Arg Gly Pro Cys Ser Pro
        35                  40                  45

Asn Pro Cys Tyr Asn Asp Ala Lys Cys Leu Val Thr Leu Asp Thr Gln
50                  55                  60

Arg Gly Asp Ile Phe Thr Glu Tyr Ile Cys Gln Cys Pro Val Gly Tyr
65                  70                  75                  80

Ser Gly Ile His Cys Glu Thr Gly Cys Ser Thr Gln Leu Gly Met Glu
                85                  90                  95

Gly Gly Ala Ile Ala Asp Ser Gln Ile Ser Ala Ser Ser Val Tyr Met
            100                 105                 110

Gly Phe Met Gly Leu Gln Arg Trp Gly Pro Glu Leu Ala Arg Leu Tyr
        115                 120                 125

Arg Thr Gly Ile Val Asn Ala Trp Thr Ala Ser Asn Tyr Asp Ser Lys
130                 135                 140

Pro Trp Ile Gln Val Asn Leu Leu Arg Lys Met Arg Val Ser Gly Val
145                 150                 155                 160

Met Thr Gln Gly Ala Ser Arg Ala Gly Arg Ala Glu Tyr Leu Lys Thr
                165                 170                 175

Phe Lys Val Ala Tyr Ser Leu Asp Gly Arg Lys Phe Glu Phe Ile Gln
            180                 185                 190

Asp Glu Ser Gly Gly Asp Lys Glu Phe Leu Gly Asn Leu Asp Asn Asn
        195                 200                 205

Ser Leu Lys Val Asn Met Phe Asn Pro Thr Leu Glu Ala Gln Tyr Ile
210                 215                 220

Arg Leu Tyr Pro Val Ser Cys His Arg Gly Cys Thr Leu Arg Phe Glu
225                 230                 235                 240

Leu Leu Gly Cys Glu Leu His Gly Cys Ser Glu Pro Leu Gly Leu Lys
                245                 250                 255

Asn Asn Thr Ile Pro Asp Ser Gln Met Ser Ala Ser Ser Tyr Lys
            260                 265                 270
```

-continued

```
Thr Trp Asn Leu Arg Ala Phe Gly Trp Tyr Pro His Leu Gly Arg Leu
        275                 280                 285

Asp Asn Gln Gly Lys Ile Asn Ala Trp Thr Ala Gln Ser Asn Ser Ala
290                 295                 300

Lys Glu Trp Leu Gln Val Asp Leu Gly Thr Gln Arg Gln Val Thr Gly
305                 310                 315                 320

Ile Ile Thr Gln Gly Ala Arg Asp Phe Gly His Ile Gln Tyr Val Ala
                325                 330                 335

Ser Tyr Lys Val Ala His Ser Asp Gly Val Gln Trp Thr Val Tyr
                340                 345                 350

Glu Glu Gln Gly Ser Ser Lys Val Phe Gln Gly Asn Leu Asp Asn Asn
            355                 360                 365

Ser His Lys Lys Asn Ile Phe Glu Lys Pro Phe Met Ala Arg Tyr Val
        370                 375                 380

Arg Val Leu Pro Val Ser Trp His Asn Arg Ile Thr Leu Arg Leu Glu
385                 390                 395                 400

Leu Leu Gly Cys

<210> SEQ ID NO 4
<211> LENGTH: 244
<212> TYPE: PRT
<213> ORGANISM: artificial
<220> FEATURE:
<223> OTHER INFORMATION: EEC - recombinant protein

<400> SEQUENCE: 4

Ala Ser Gly Asp Phe Cys Asp Ser Ser Leu Cys Leu Asn Gly Gly Thr
1               5                   10                  15

Cys Leu Thr Gly Gln Asp Asn Asp Ile Tyr Cys Leu Cys Pro Glu Gly
            20                  25                  30

Phe Thr Gly Leu Val Cys Asn Glu Thr Glu Arg Gly Pro Cys Ser Pro
        35                  40                  45

Asn Pro Cys Tyr Asn Asp Ala Lys Cys Leu Val Thr Leu Asp Thr Gln
50                  55                  60

Arg Gly Asp Ile Phe Thr Glu Tyr Ile Cys Gln Cys Pro Val Gly Tyr
65                  70                  75                  80

Ser Gly Ile His Cys Glu Thr Gly Cys Ser Thr Gln Leu Gly Met Glu
                85                  90                  95

Gly Gly Ala Ile Ala Asp Ser Gln Ile Ser Ala Ser Ser Val Tyr Met
            100                 105                 110

Gly Phe Met Gly Leu Gln Arg Trp Gly Pro Glu Leu Ala Arg Leu Tyr
        115                 120                 125

Arg Thr Gly Ile Val Asn Ala Trp Thr Ala Ser Asn Tyr Asp Ser Lys
130                 135                 140

Pro Trp Ile Gln Val Asn Leu Leu Arg Lys Met Arg Val Ser Gly Val
145                 150                 155                 160

Met Thr Gln Gly Ala Ser Arg Ala Gly Arg Ala Glu Tyr Leu Lys Thr
                165                 170                 175

Phe Lys Val Ala Tyr Ser Leu Asp Gly Arg Lys Phe Glu Phe Ile Gln
            180                 185                 190

Asp Glu Ser Gly Gly Asp Lys Glu Phe Leu Gly Asn Leu Asp Asn Asn
        195                 200                 205

Ser Leu Lys Val Asn Met Phe Asn Pro Thr Leu Glu Ala Gln Tyr Ile
210                 215                 220
```

```
Arg Leu Tyr Pro Val Ser Cys His Arg Gly Cys Thr Leu Arg Phe Glu
225                 230                 235                 240

Leu Leu Gly Cys

<210> SEQ ID NO 5
<211> LENGTH: 365
<212> TYPE: PRT
<213> ORGANISM: artificial
<220> FEATURE:
<223> OTHER INFORMATION: ECC - recombinant protein

<400> SEQUENCE: 5

Glu Thr Glu Arg Gly Pro Cys Ser Pro Asn Pro Cys Tyr Asn Asp Ala
1               5                   10                  15

Lys Cys Leu Val Thr Leu Asp Thr Gln Arg Gly Asp Ile Phe Thr Glu
            20                  25                  30

Tyr Ile Cys Gln Cys Pro Val Gly Tyr Ser Gly Ile His Cys Glu Thr
        35                  40                  45

Gly Cys Ser Thr Gln Leu Gly Met Glu Gly Gly Ala Ile Ala Asp Ser
    50                  55                  60

Gln Ile Ser Ala Ser Ser Val Tyr Met Gly Phe Met Gly Leu Gln Arg
65                  70                  75                  80

Trp Gly Pro Glu Leu Ala Arg Leu Tyr Arg Thr Gly Ile Val Asn Ala
                85                  90                  95

Trp Thr Ala Ser Asn Tyr Asp Ser Lys Pro Trp Ile Gln Val Asn Leu
            100                 105                 110

Leu Arg Lys Met Arg Val Ser Gly Val Met Thr Gln Gly Ala Ser Arg
        115                 120                 125

Ala Gly Arg Ala Glu Tyr Leu Lys Thr Phe Lys Val Ala Tyr Ser Leu
    130                 135                 140

Asp Gly Arg Lys Phe Glu Phe Ile Gln Asp Glu Ser Gly Gly Asp Lys
145                 150                 155                 160

Glu Phe Leu Gly Asn Leu Asp Asn Asn Ser Leu Lys Val Asn Met Phe
                165                 170                 175

Asn Pro Thr Leu Glu Ala Gln Tyr Ile Arg Leu Tyr Pro Val Ser Cys
            180                 185                 190

His Arg Gly Cys Thr Leu Arg Phe Glu Leu Leu Gly Cys Glu Leu His
        195                 200                 205

Gly Cys Ser Glu Pro Leu Gly Leu Lys Asn Asn Thr Ile Pro Asp Ser
    210                 215                 220

Gln Met Ser Ala Ser Ser Tyr Lys Thr Trp Asn Leu Arg Ala Phe
225                 230                 235                 240

Gly Trp Tyr Pro His Leu Gly Arg Leu Asp Asn Gln Gly Lys Ile Asn
                245                 250                 255

Ala Trp Thr Ala Gln Ser Asn Ser Ala Lys Glu Trp Leu Gln Val Asp
            260                 265                 270

Leu Gly Thr Gln Arg Gln Val Thr Gly Ile Ile Thr Gln Gly Ala Arg
        275                 280                 285

Asp Phe Gly His Ile Gln Tyr Val Ala Ser Tyr Lys Val Ala His Ser
    290                 295                 300

Asp Asp Gly Val Gln Trp Thr Val Tyr Glu Glu Gln Gly Ser Ser Lys
305                 310                 315                 320

Val Phe Gln Gly Asn Leu Asp Asn Asn Ser His Lys Lys Asn Ile Phe
                325                 330                 335

Glu Lys Pro Phe Met Ala Arg Tyr Val Arg Val Leu Pro Val Ser Trp
```

```
                    340                 345                 350
His Asn Arg Ile Thr Leu Arg Leu Glu Leu Leu Gly Cys
        355                 360                 365

<210> SEQ ID NO 6
<211> LENGTH: 205
<212> TYPE: PRT
<213> ORGANISM: artificial
<220> FEATURE:
<223> OTHER INFORMATION: EC - recombinant protein

<400> SEQUENCE: 6

Glu Thr Glu Arg Gly Pro Cys Ser Pro Asn Pro Cys Tyr Asn Asp Ala
1               5                   10                  15

Lys Cys Leu Val Thr Leu Asp Thr Gln Arg Gly Asp Ile Phe Thr Glu
            20                  25                  30

Tyr Ile Cys Gln Cys Pro Val Gly Tyr Ser Gly Ile His Cys Glu Thr
        35                  40                  45

Gly Cys Ser Thr Gln Leu Gly Met Glu Gly Gly Ala Ile Ala Asp Ser
    50                  55                  60

Gln Ile Ser Ala Ser Ser Val Tyr Met Gly Phe Met Gly Leu Gln Arg
65                  70                  75                  80

Trp Gly Pro Glu Leu Ala Arg Leu Tyr Arg Thr Gly Ile Val Asn Ala
                85                  90                  95

Trp Thr Ala Ser Asn Tyr Asp Ser Lys Pro Trp Ile Gln Val Asn Leu
            100                 105                 110

Leu Arg Lys Met Arg Val Ser Gly Val Met Thr Gln Gly Ala Ser Arg
        115                 120                 125

Ala Gly Arg Ala Glu Tyr Leu Lys Thr Phe Lys Val Ala Tyr Ser Leu
    130                 135                 140

Asp Gly Arg Lys Phe Glu Phe Ile Gln Asp Glu Ser Gly Gly Asp Lys
145                 150                 155                 160

Glu Phe Leu Gly Asn Leu Asp Asn Asn Ser Leu Lys Val Asn Met Phe
                165                 170                 175

Asn Pro Thr Leu Glu Ala Gln Tyr Ile Arg Leu Tyr Pro Val Ser Cys
            180                 185                 190

His Arg Gly Cys Thr Leu Arg Phe Glu Leu Leu Gly Cys
        195                 200                 205

<210> SEQ ID NO 7
<211> LENGTH: 317
<212> TYPE: PRT
<213> ORGANISM: artificial
<220> FEATURE:
<223> OTHER INFORMATION: CC - recombinant protein

<400> SEQUENCE: 7

Gly Cys Ser Thr Gln Leu Gly Met Glu Gly Gly Ala Ile Ala Asp Ser
1               5                   10                  15

Gln Ile Ser Ala Ser Ser Val Tyr Met Gly Phe Met Gly Leu Gln Arg
            20                  25                  30

Trp Gly Pro Glu Leu Ala Arg Leu Tyr Arg Thr Gly Ile Val Asn Ala
        35                  40                  45

Trp Thr Ala Ser Asn Tyr Asp Ser Lys Pro Trp Ile Gln Val Asn Leu
    50                  55                  60

Leu Arg Lys Met Arg Val Ser Gly Val Met Thr Gln Gly Ala Ser Arg
65                  70                  75                  80
```

```
Ala Gly Arg Ala Glu Tyr Leu Lys Thr Phe Lys Val Ala Tyr Ser Leu
            85                  90                  95

Asp Gly Arg Lys Phe Glu Phe Ile Gln Asp Glu Ser Gly Gly Asp Lys
            100                 105                 110

Glu Phe Leu Gly Asn Leu Asp Asn Asn Ser Leu Lys Val Asn Met Phe
            115                 120                 125

Asn Pro Thr Leu Glu Ala Gln Tyr Ile Arg Leu Tyr Pro Val Ser Cys
130                 135                 140

His Arg Gly Cys Thr Leu Arg Phe Glu Leu Leu Gly Cys Glu Leu His
145                 150                 155                 160

Gly Cys Ser Glu Pro Leu Gly Leu Lys Asn Asn Thr Ile Pro Asp Ser
                165                 170                 175

Gln Met Ser Ala Ser Ser Ser Tyr Lys Thr Trp Asn Leu Arg Ala Phe
            180                 185                 190

Gly Trp Tyr Pro His Leu Gly Arg Leu Asp Asn Gln Gly Lys Ile Asn
            195                 200                 205

Ala Trp Thr Ala Gln Ser Asn Ser Ala Lys Glu Trp Leu Gln Val Asp
            210                 215                 220

Leu Gly Thr Gln Arg Gln Val Thr Gly Ile Ile Thr Gln Gly Ala Arg
225                 230                 235                 240

Asp Phe Gly His Ile Gln Tyr Val Ala Ser Tyr Lys Val Ala His Ser
                245                 250                 255

Asp Asp Gly Val Gln Trp Thr Val Tyr Glu Glu Gln Gly Ser Ser Lys
            260                 265                 270

Val Phe Gln Gly Asn Leu Asp Asn Asn Ser His Lys Lys Asn Ile Phe
            275                 280                 285

Glu Lys Pro Phe Met Ala Arg Tyr Val Arg Val Leu Pro Val Ser Trp
            290                 295                 300

His Asn Arg Ile Thr Leu Arg Leu Glu Leu Leu Gly Cys
305                 310                 315

<210> SEQ ID NO 8
<211> LENGTH: 25
<212> TYPE: DNA
<213> ORGANISM: artificial sequence
<220> FEATURE:
<223> OTHER INFORMATION: primer sequence

<400> SEQUENCE: 8
cctcaggctg aggactggca gcggc                                    25

<210> SEQ ID NO 9
<211> LENGTH: 26
<212> TYPE: DNA
<213> ORGANISM: artificial sequence
<220> FEATURE:
<223> OTHER INFORMATION: primer sequence

<400> SEQUENCE: 9
gctgtcaccg ggtgtccagg gtcacc                                   26
```